US012098167B2

(12) United States Patent
Zeng et al.

(10) Patent No.: US 12,098,167 B2
(45) Date of Patent: Sep. 24, 2024

(54) SELF-ASSEMBLED NANOPARTICLE CONTAINING GB PROTEIN OF EB VIRUS AND PREPARATION METHOD AND USE THEREOF

(71) Applicants: SUN YAT-SEN UNIVERSITY, Guangdong (CN); SUN YAT-SEN UNIVERSITY CANCER CENTER (SYSUCC), Guangdong (CN)

(72) Inventors: Musheng Zeng, Guangdong (CN); Cong Sun, Guangdong (CN); Yixin Zeng, Guangdong (CN); Guokai Feng, Guangdong (CN); Yinfeng Kang, Guangdong (CN); Xinchun Chen, Guangdong (CN); Xiao Zhang, Guangdong (CN); Qianying Zhu, Guangdong (CN); Jiangping Li, Guangdong (CN); Xiangwei Kong, Guangdong (CN)

(73) Assignees: SUN YAT-SEN UNIVERSITY, Guangdong (CN); SUN YAT-SEN UNIVERSITY CANCER CENTER (SYSUCC), Guangdong (CN)

( * ) Notice: Subject to any disclaimer, the term of this patent is extended or adjusted under 35 U.S.C. 154(b) by 0 days.

(21) Appl. No.: 17/762,308

(22) PCT Filed: Dec. 15, 2020

(86) PCT No.: PCT/CN2020/136752
§ 371 (c)(1),
(2) Date: Mar. 21, 2022

(87) PCT Pub. No.: WO2022/120908
PCT Pub. Date: Jun. 16, 2022

(65) Prior Publication Data
US 2024/0034755 A1 Feb. 1, 2024

(30) Foreign Application Priority Data
Dec. 7, 2020 (CN) .......................... 202011417091.0

(51) Int. Cl.
*C07K 14/05* (2006.01)
*A61K 9/51* (2006.01)
*A61K 39/00* (2006.01)
*A61K 39/245* (2006.01)
*A61P 31/22* (2006.01)

(52) U.S. Cl.
CPC .............. *C07K 14/05* (2013.01); *A61K 9/51* (2013.01); *A61K 39/245* (2013.01); *A61P 31/22* (2018.01); *A61K 2039/55555* (2013.01)

(58) Field of Classification Search
CPC .................. C07K 14/05; C07K 14/005; C07K 2319/00; A61K 9/51; A61K 39/245; A61K 2039/55555; A61K 2039/55566; A61K 2039/575; A61K 39/12; A61K 38/162; A61P 31/22; C12N 2710/16234; C12N 2710/16222; Y02A 50/30
See application file for complete search history.

(56) References Cited

U.S. PATENT DOCUMENTS

| | | | |
|---|---|---|---|
| 2005/0228074 A1 | 10/2005 | Warren et al. | |
| 2008/0302271 A1 | 12/2008 | Carlini et al. | |
| 2016/0303224 A1* | 10/2016 | Kanekiyo | ............ C07K 16/085 |
| 2020/0397886 A1* | 12/2020 | King | ....................... C12N 15/86 |

FOREIGN PATENT DOCUMENTS

| | | |
|---|---|---|
| CN | 102108336 A | 6/2011 |
| CN | 105518149 A | 4/2016 |
| CN | 110615848 A | 12/2019 |
| CN | 110678208 A | 1/2020 |
| CN | 110922488 A | 3/2020 |
| CN | 111333733 A | 6/2020 |

(Continued)

OTHER PUBLICATIONS

Zhang X, Zhao B, Ding M, Song S, Kang Y, Yu Y, Xu M, Xiang T, Gao L, Feng Q, et. al a novel vaccine candidate based on chimeric virus-like particle displaying multiple conserved epitope peptides induced neutralizing antibodies against EBV infection. Theranostics. Apr. 27, 2020;10(13):5704-5718. (Year: 2020).*
Brouwer, P.J.M. et al. Enhancing and shaping the immunogenicity of native-like HIV-1 envelope trimers with a two-component protein nanoparticle Nat. Commun. Sep. 19, 2019(Sep. 19, 2019), No. 10, vol. 1, Abstract, the last paragraph of the right column on p. 2.
Wei B. et al. Immunization with Components of the Viral Fusion Apparatus Elicits Antibodies That Neutralize Epstein-Barr Virus in B Cells and Epithelial Cells Immunity May 21, 2019(May 21, 2019), pp. 1305-1316.
Huang JD, Huang K. Recent progress in bio-engineered nanoparticles for Epstein-Barr virus vaccines [J]. Journal of Integration Technology, 2021, 10(4): 67-77.

(Continued)

*Primary Examiner* — Rachel B Gill
(74) *Attorney, Agent, or Firm* — D'Ambrosio & Menon, PLLC; Usha Menon

(57) ABSTRACT

The present invention is related to a self-assembled nanoparticle containing a gB protein of an EB virus and a preparation method and use thereof. The self-assembled nanoparticle comprises a first polypeptide and a second polypeptide; the first polypeptide comprises the gB protein and a first vector subunit, the second polypeptide comprises a second vector subunit; the first vector subunit is I53-50A1, and the second vector subunit is I53-50B.4PT1. In the self-assembled nanoparticle, the gB protein of the EB virus is displayed on the surface of the nanoparticle for the first time. The particle size of the self-assembled nanoparticle is larger than that of the antigen gB, and the chemical stability of the self-assembled nanoparticle is higher than that of the antigen gB, and the binding capacity with the neutralizing antibody of the self-assembled nanoparticle are higher than that of the antigen gB.

15 Claims, 9 Drawing Sheets
Specification includes a Sequence Listing.

(56) References Cited

FOREIGN PATENT DOCUMENTS

| | | | |
|---|---|---|---|
| CN | 111991556 | A | 11/2020 |
| CN | 112521511 | B | 3/2023 |
| EP | 2630967 | A1 | 8/2013 |
| WO | 2019079215 | A1 | 4/2019 |
| WO | 2019161163 | A1 | 8/2019 |
| WO | 2019169120 | A1 | 9/2019 |

OTHER PUBLICATIONS

First notice of examination opinions for CN2020114170910 dated Apr. 18, 2022.
Notification of grant of patent right for invention for CN2020114170910 dated Jan. 29, 2023.

\* cited by examiner

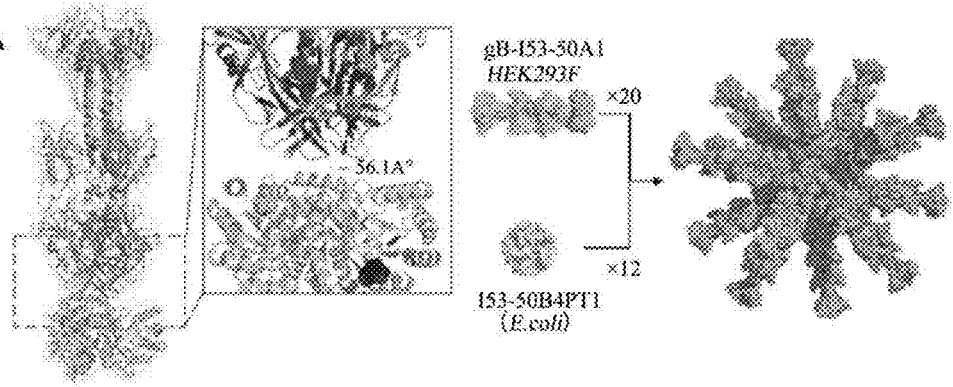
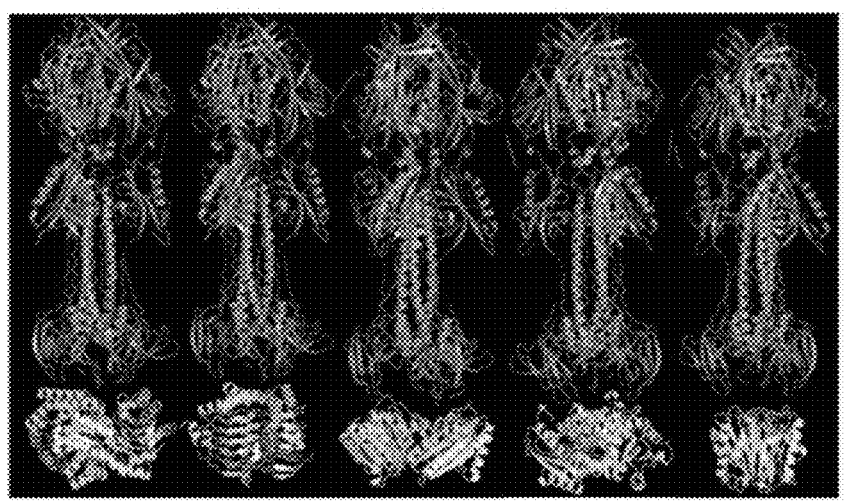

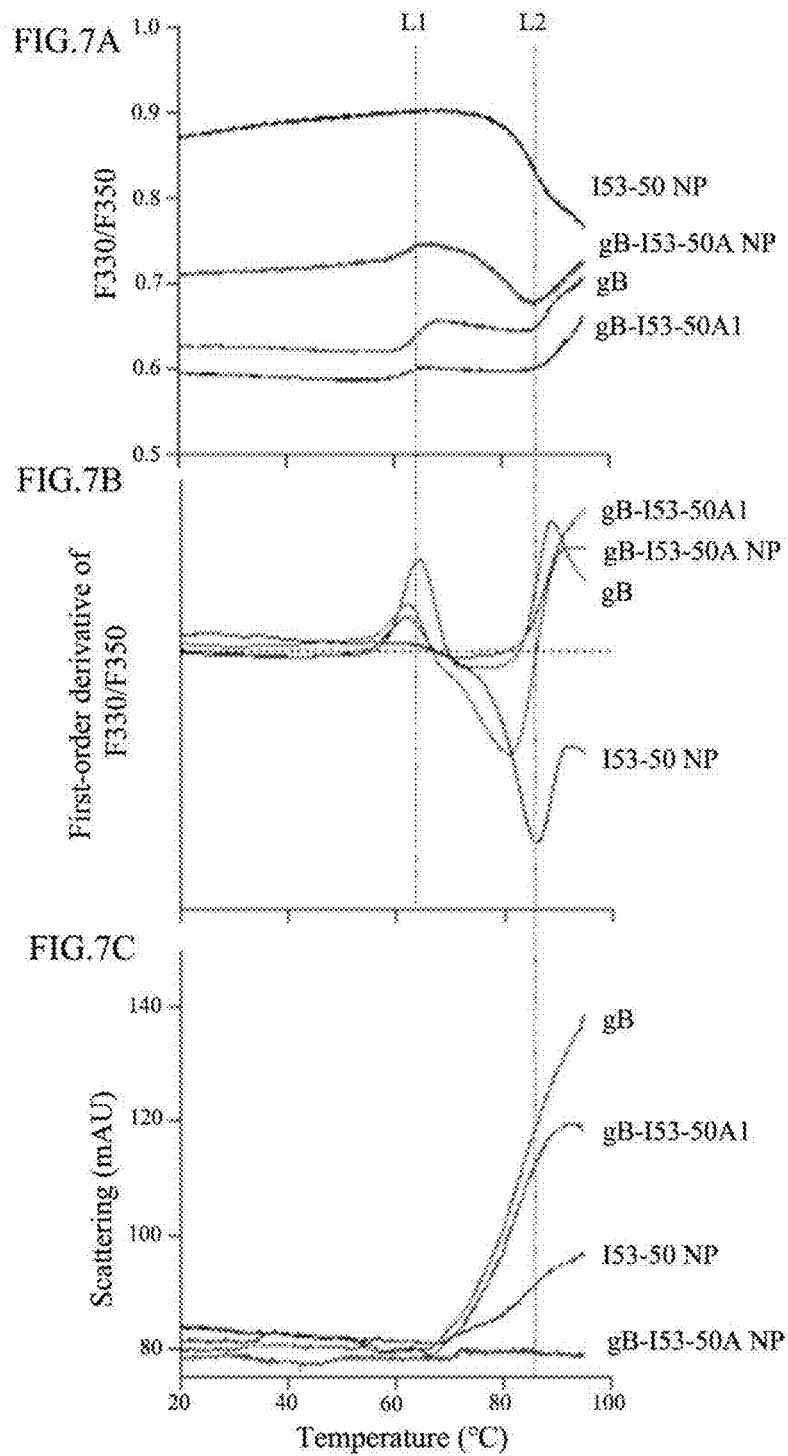

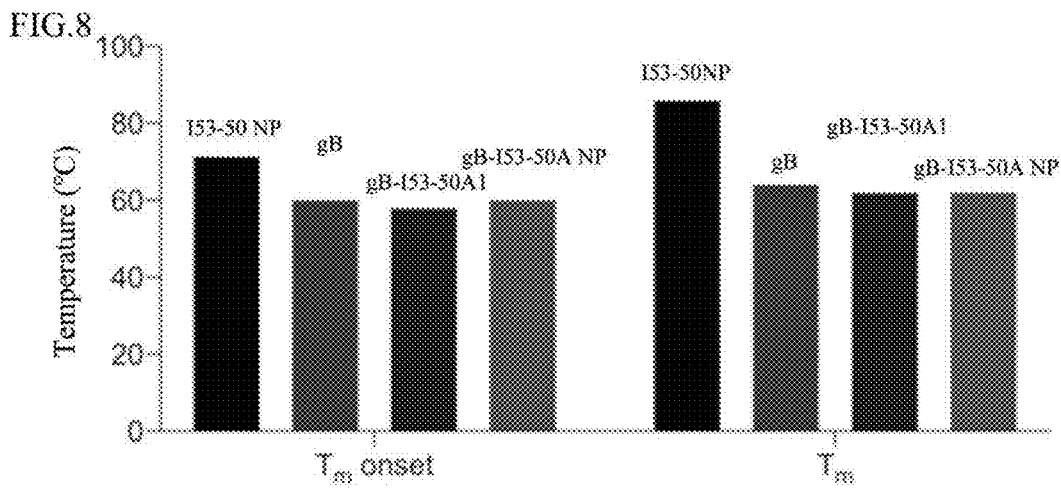
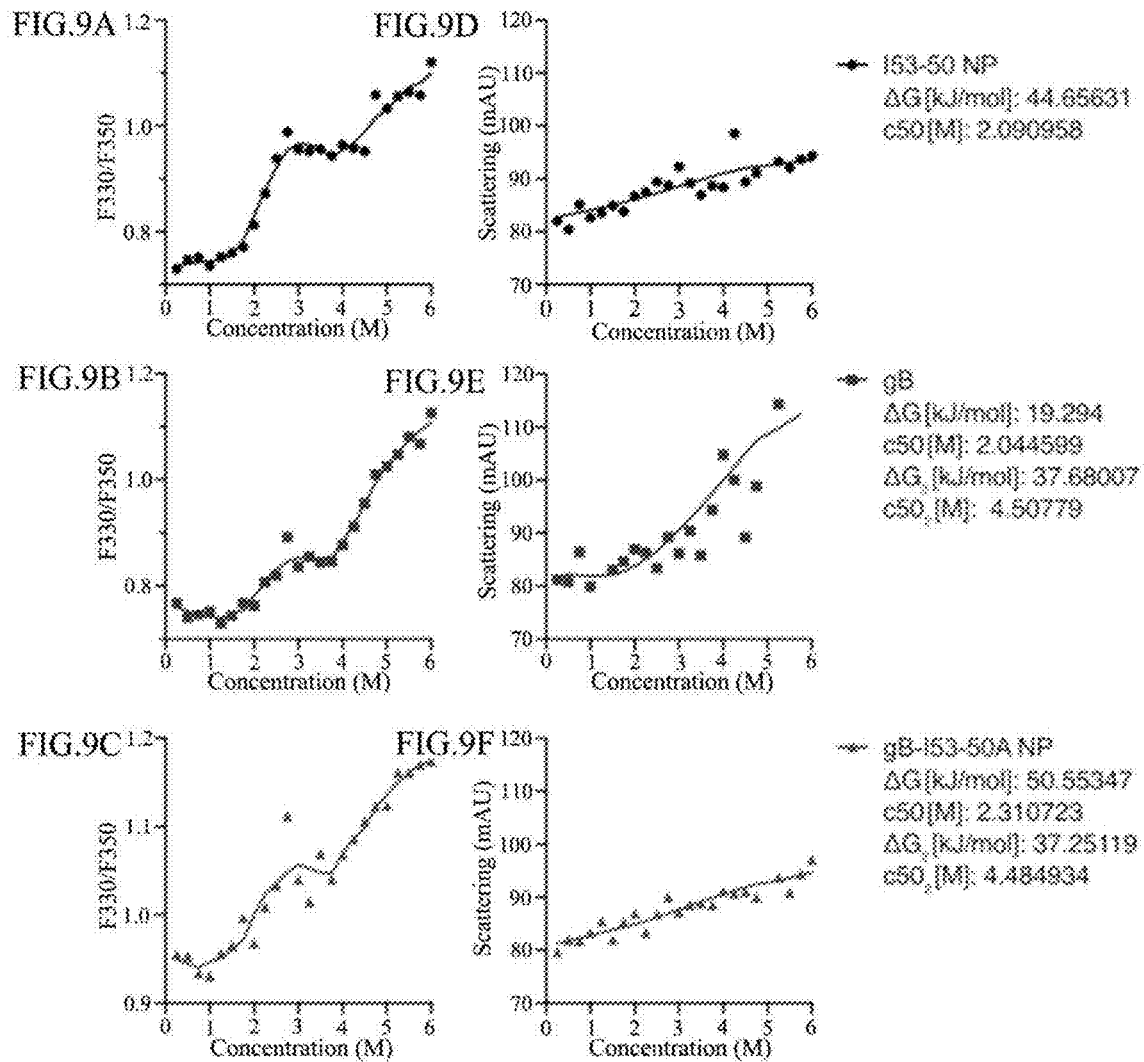

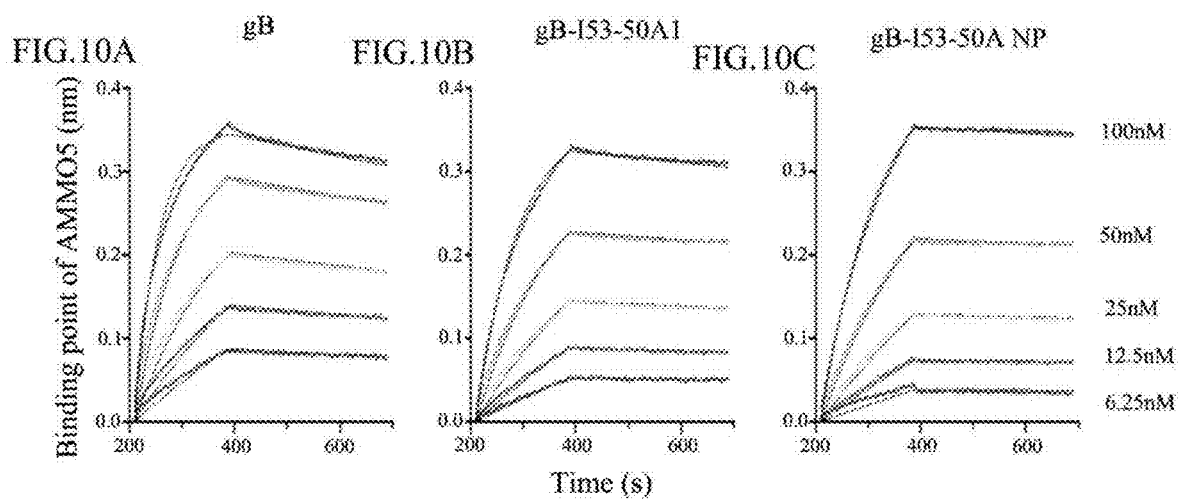

SEQUENCE LISTING

```
<160> NUMBER OF SEQ ID NOS: 29

<210> SEQ ID NO 1
<211> LENGTH: 209
<212> TYPE: PRT
<213> ORGANISM: Artificial Sequence
<220> FEATURE:
<223> OTHER INFORMATION: synthesized

<400> SEQUENCE: 1

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Asp Ala Leu Val Lys Gly Asp Pro Asp Glu Val Arg Glu Lys
            180                 185                 190

Ala Lys Lys Phe Val Glu Lys Ile Arg Gly Cys Thr Glu Gly Ser Leu
        195                 200                 205

Glu

<210> SEQ ID NO 2
<211> LENGTH: 160
<212> TYPE: PRT
<213> ORGANISM: Artificial Sequence
<220> FEATURE:
<223> OTHER INFORMATION: synthesized

<400> SEQUENCE: 2

Met Asn Gln His Ser His Lys Asp His Glu Thr Val Arg Ile Ala Val
1               5                   10                  15
```

-continued

```
Val Arg Ala Arg Trp His Ala Glu Ile Val Asp Ala Cys Val Ser Ala
                20                  25                  30

Phe Glu Ala Ala Met Arg Asp Ile Gly Gly Asp Arg Phe Ala Val Asp
         35                  40                  45

Val Phe Asp Val Pro Gly Ala Tyr Glu Ile Pro Leu His Ala Arg Thr
 50                  55                  60

Leu Ala Glu Thr Gly Arg Tyr Gly Ala Val Leu Gly Thr Ala Phe Val
 65                  70                  75                  80

Val Asn Gly Gly Ile Tyr Arg His Glu Phe Val Ala Ser Ala Val Ile
                 85                  90                  95

Asn Gly Met Met Asn Val Gln Leu Asn Thr Gly Val Pro Val Leu Ser
            100                 105                 110

Ala Val Leu Thr Pro His Asn Tyr Asp Lys Ser Lys Ala His Thr Leu
        115                 120                 125

Leu Phe Leu Ala Leu Phe Ala Val Lys Gly Met Glu Ala Ala Arg Ala
130                 135                 140

Cys Val Glu Ile Leu Ala Ala Arg Glu Lys Ile Ala Ala Gly Ser Leu
145                 150                 155                 160

<210> SEQ ID NO 3
<211> LENGTH: 661
<212> TYPE: PRT
<213> ORGANISM: Epstein-Barr Virus

<400> SEQUENCE: 3

Gln Thr Pro Glu Gln Pro Ala Pro Pro Ala Thr Thr Val Gln Pro Thr
1               5                   10                  15

Ala Thr Arg Gln Gln Thr Ser Phe Pro Phe Arg Val Cys Glu Leu Ser
                20                  25                  30

Ser His Gly Asp Leu Phe Arg Phe Ser Ser Asp Ile Gln Cys Pro Ser
            35                  40                  45

Phe Gly Thr Arg Glu Asn His Thr Glu Gly Leu Leu Met Val Phe Lys
        50                  55                  60

Asp Asn Ile Ile Pro Tyr Ser Phe Lys Val Arg Ser Tyr Thr Lys Ile
65                  70                  75                  80

Val Thr Asn Ile Leu Ile Tyr Asn Gly His Arg Ala Asp Ser Val Thr
                85                  90                  95

Asn Arg His Glu Glu Lys Phe Ser Val Glu Ser Tyr Glu Thr Asp Gln
            100                 105                 110

Met Asp Thr Ile Tyr Gln Cys Tyr Asn Ala Val Lys Met Thr Lys Asp
        115                 120                 125

Gly Leu Thr Arg Val Tyr Val Asp Arg Asp Gly Val Asn Ile Thr Val
130                 135                 140

Asn Leu Lys Pro Thr Gly Gly Leu Ala Asn Gly Val Arg Arg Tyr Ala
145                 150                 155                 160

Ser Gln Thr Glu Leu Tyr Asp Ala Pro Gly Arg Val Glu Ala Thr Tyr
                165                 170                 175

Arg Thr Arg Thr Thr Val Asn Cys Leu Ile Thr Asp Met Met Ala Lys
            180                 185                 190

Ser Asn Ser Pro Phe Asp Phe Phe Val Thr Thr Thr Gly Gln Thr Val
        195                 200                 205

Glu Met Ser Pro Phe Tyr Asp Gly Lys Asn Thr Glu Thr Phe His Glu
210                 215                 220

Arg Ala Asp Ser Phe His Val Arg Thr Asn Tyr Lys Ile Val Asp Tyr
225                 230                 235                 240
```

-continued

Asp Asn Arg Gly Thr Asn Pro Gln Gly Glu Arg Arg Ala Phe Leu Asp
            245                 250                 255
Lys Gly Thr Tyr Thr Leu Ser Trp Lys Leu Glu Asn Arg Thr Ala Tyr
            260                 265                 270
Cys Pro Leu Gln His Trp Gln Thr Phe Asp Ser Thr Ile Ala Thr Glu
            275                 280                 285
Thr Gly Lys Ser Ile His Phe Val Thr Asp Glu Gly Thr Ser Ser Phe
            290                 295                 300
Val Thr Asn Thr Thr Val Gly Ile Glu Leu Pro Asp Ala Phe Lys Cys
305                 310                 315                 320
Ile Glu Glu Gln Val Asn Lys Thr Met His Glu Lys Tyr Glu Ala Val
                325                 330                 335
Gln Asp Arg Tyr Thr Lys Gly Gln Glu Ala Ile Thr Tyr Phe Ile Thr
            340                 345                 350
Ser Gly Gly Leu Leu Leu Ala Trp Leu Pro Leu Thr Pro Arg Ser Leu
            355                 360                 365
Ala Thr Val Lys Asn Leu Thr Glu Leu Thr Thr Pro Thr Ser Ser Pro
            370                 375                 380
Pro Ser Ser Pro Ser Pro Pro Ala Pro Pro Ala Ala Arg Gly Ser Thr
385                 390                 395                 400
Ser Ala Ala Val Leu Arg Arg Arg Arg Asn Ala Gly Asn Ala Thr
                405                 410                 415
Thr Pro Val Pro Pro Ala Ala Pro Gly Lys Ser Leu Gly Thr Leu Asn
            420                 425                 430
Asn Pro Ala Thr Val Gln Ile Gln Phe Ala Tyr Asp Ser Leu Arg Arg
            435                 440                 445
Gln Ile Asn Arg Met Leu Gly Asp Leu Ala Arg Ala Trp Cys Leu Glu
            450                 455                 460
Gln Lys Arg Gln Asn Met Val Leu Arg Glu Leu Thr Lys Ile Asn Pro
465                 470                 475                 480
Thr Thr Val Met Ser Ser Ile Tyr Gly Lys Ala Val Ala Ala Lys Arg
                485                 490                 495
Leu Gly Asp Val Ile Ser Val Ser Gln Cys Val Pro Val Asn Gln Ala
            500                 505                 510
Thr Val Thr Leu Arg Lys Ser Met Arg Val Pro Gly Ser Glu Thr Met
            515                 520                 525
Cys Tyr Ser Arg Pro Leu Val Ser Phe Ser Phe Ile Asn Asp Thr Lys
            530                 535                 540
Thr Tyr Glu Gly Gln Leu Gly Thr Asp Asn Glu Ile Phe Leu Thr Lys
545                 550                 555                 560
Lys Met Thr Glu Val Cys Gln Ala Thr Ser Gln Tyr Tyr Phe Gln Ser
                565                 570                 575
Gly Asn Glu Ile His Val Tyr Asn Asp Tyr His His Phe Lys Thr Ile
            580                 585                 590
Glu Leu Asp Gly Ile Ala Thr Leu Gln Thr Phe Ile Ser Leu Asn Thr
            595                 600                 605
Ser Leu Ile Glu Asn Ile Asp Phe Ala Ser Leu Glu Leu Tyr Ser Arg
            610                 615                 620
Asp Glu Gln Arg Ala Ser Asn Val Phe Asp Leu Glu Gly Ile Phe Arg
625                 630                 635                 640
Glu Tyr Asn Phe Gln Ala Gln Asn Ile Ala Gly Leu Arg Lys Asp Leu
                645                 650                 655

Asp Asn Ala Val Ser
            660

<210> SEQ ID NO 4
<211> LENGTH: 10
<212> TYPE: PRT
<213> ORGANISM: Artificial Sequence
<220> FEATURE:
<223> OTHER INFORMATION: synthesized

<400> SEQUENCE: 4

Gly Gly Gly Gly Ser Gly Gly Gly Gly Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthesized

<400> SEQUENCE: 5

Gly Gly Gly Gly Ser Gly Gly Gly Gly Ser Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthesized

<400> SEQUENCE: 6

Gly Gly Gly Gly Ser Gly Gly Gly Gly Ser Gly Ser
1               5                   10

<210> SEQ ID NO 7
<211> LENGTH: 13
<212> TYPE: PRT
<213> ORGANISM: Artificial Sequence
<220> FEATURE:
<223> OTHER INFORMATION: synthesized

<400> SEQUENCE: 7

Gly Gly Gly Gly Ser Gly Gly Gly Ser Gly Gly Ser
1               5                   10

<210> SEQ ID NO 8
<211> LENGTH: 14
<212> TYPE: PRT
<213> ORGANISM: Artificial Sequence
<220> FEATURE:
<223> OTHER INFORMATION: synthesized

<400> SEQUENCE: 8

Gly Gly Gly Gly Ser Gly Gly Gly Gly Ser Gly Gly Gly Ser
1               5                   10

<210> SEQ ID NO 9
<211> LENGTH: 15
<212> TYPE: PRT
<213> ORGANISM: Artificial Sequence
<220> FEATURE:
<223> OTHER INFORMATION: synthesized

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 27
<212> TYPE: PRT
<213> ORGANISM: Artificial Sequence
<220> FEATURE:
<223> OTHER INFORMATION: synthesized

<400> SEQUENCE: 10

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 11
<211> LENGTH: 32
<212> TYPE: PRT
<213> ORGANISM: Artificial Sequence
<220> FEATURE:
<223> OTHER INFORMATION: synthesized

<400> SEQUENCE: 11

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Val
            20                  25                  30

<210> SEQ ID NO 12
<211> LENGTH: 1983
<212> TYPE: DNA
<213> ORGANISM: Epstein-Barr Virus

<400> SEQUENCE: 12

| | | |
|---|---|---|
| cagacccag agcagcctgc accacctgcc accacagtgc agcctacagc caccagacag | 60 |
| cagaccagct tccccttccg ggtgtgcgag ctgagctccc acggcgacct gttcagattt | 120 |
| tctagcgata tccagtgtcc ctccttcggc acaagggaga accacaccga gggcctgctg | 180 |
| atggtgttca aggacaatat catcccttac tcctttaagg tgagatctta tacaaagatc | 240 |
| gtgaccaaca tcctgatcta caatggccac agagccgatt ctgtgaccaa caggcacgag | 300 |
| gagaagttta gcgtggagtc ctatgagaca gaccagatgg ataccatcta ccagtgctat | 360 |
| aatgccgtga agatgacaaa ggacggcctg accagagtgt acgtggacag ggatggcgtg | 420 |
| aacatcacag tgaatctgaa gcctaccgga ggactggcaa acggcgtgcg agatacgcc | 480 |
| agccagaccg agctgtatga tgcaccagga agggtggagg caacatacag gaccaggacc | 540 |
| acagtgaact gtctgatcac agacatgatg gccaagagca attccccatt cgatttcttt | 600 |
| gtgaccacaa ccggccagac cgtggagatg agccccttt atgacggcaa gaacacagag | 660 |
| accttccacg agcgcgccga ttcctttcac gtgcggacaa attacaagat cgtggactat | 720 |
| gataacagag gaccaatcc acagggagag aggagggcct tcctggacaa gggcacatac | 780 |
| accctgtcct ggaagctgga gaacaggaca gcctattgcc ccctgcagca ctggcagaca | 840 |
| tttgactcca ccatcgccac agagaccggc aagtctatcc acttcgtgac agatgagggc | 900 |
| acctcctctt ttgtgaccaa cacaaccgtg gcatcgagc tgcccgacgc cttcaagtgt | 960 |
| atcgaggagc aagtgaataa gacaatgcac gagaagtacg aggccgtgca ggatcgctat | 1020 |

-continued

```
accaagggcc aggaagccat cacatacttt atcaccagcg gaggactgct gctggcatgg    1080
ctgccactga caccacggtc cctggccaca gtgaagaatc tgaccgagct gacaaccca     1140 accagctccc caccatctag cccaagccct ccagcaccac ctgcagcacg gggctctacc    1200
agcgccgccg tgctgcggag aaggcgccgg aacgcaggaa atgcaacaac ccctgtgcca    1260
ccagcagcac ctggcaagtc tctgggcaca ctgaacaatc cgccaccgt gcagatccag     1320 ttcgcctacg acagcctgag aaggcagatc aacagaatgc tgggcgatct ggcaagggca    1380
tggtgcctgg agcagaagcg ccagaacatg gtgctgcggg agctgaccaa gatcaatcct    1440
acaaccgtga tgtcctctat ctatggcaag gcagtggcag caaagagact gggcgacgtg    1500
atctccgtgt ctcagtgcgt gccagtgaat caggccacag tgaccctgag aaagagcatg    1560
agggtgcccg gctccgagac catgtgctac tctaggcctc tggtgagctt ctcctttatc    1620
aacgacacaa agacctatga gggccagctg gcacagata atgagatctt cctgacaaag    1680
aagatgaccg aggtgtgcca ggccaccagc cagtactatt tccagtccgg caacgagatc    1740
cacgtgtaca atgactatca ccactttaag acaatcgagc tggatggcat cgccacactg    1800
cagaccttca tctctctgaa caccagcctg atcgagaata tcgactttgc cagcctggag    1860
ctgtactcca gggacgagca gagggcatcc aacgtgttcg atctggaggg catcttccgc    1920
gagtataact ttcaggccca gaatatcgcc ggcctgcgga aggacctgga taatgccgtg    1980
tct                                                                  1983
```

```
<210> SEQ ID NO 13
<211> LENGTH: 30
<212> TYPE: DNA
<213> ORGANISM: Artificial Sequence
<220> FEATURE:
<223> OTHER INFORMATION: synthesized

<400> SEQUENCE: 13
ggaggaggag gaagcggagg aggaggatcc                                       30

<210> SEQ ID NO 14
<211> LENGTH: 33
<212> TYPE: DNA
<213> ORGANISM: Artificial Sequence
<220> FEATURE:
<223> OTHER INFORMATION: synthesized

<400> SEQUENCE: 14
ggaggaggag gaagcggagg aggaggatcc ggc                                   33

<210> SEQ ID NO 15
<211> LENGTH: 36
<212> TYPE: DNA
<213> ORGANISM: Artificial Sequence
<220> FEATURE:
<223> OTHER INFORMATION: synthesized

<400> SEQUENCE: 15
ggaggaggag gaagcggagg aggaggatcc ggcggc                                36

<210> SEQ ID NO 16
<211> LENGTH: 39
<212> TYPE: DNA
<213> ORGANISM: Artificial Sequence
<220> FEATURE:
<223> OTHER INFORMATION: synthesized
```

<400> SEQUENCE: 16
ggaggaggag gaagcggagg aggaggatcc ggcggcggc                    39

<210> SEQ ID NO 17
<211> LENGTH: 42
<212> TYPE: DNA
<213> ORGANISM: Artificial Sequence
<220> FEATURE:
<223> OTHER INFORMATION: synthesized

<400> SEQUENCE: 17
ggaggaggag gaagcggagg aggaggatcc ggcggcggcg gc                42

<210> SEQ ID NO 18
<211> LENGTH: 45
<212> TYPE: DNA
<213> ORGANISM: Artificial Sequence
<220> FEATURE:
<223> OTHER INFORMATION: synthesized

<400> SEQUENCE: 18
ggaggaggag gaagcggagg aggaggatcc ggcggcggcg gctct             45

<210> SEQ ID NO 19
<211> LENGTH: 81
<212> TYPE: DNA
<213> ORGANISM: Artificial Sequence
<220> FEATURE:
<223> OTHER INFORMATION: synthesized

<400> SEQUENCE: 19
ggatacatcc ctgaggcacc aagggacgga caggcctatg tgcggaagga tggcgagtgg    60
gtgctgctgt ccaccttcct g                                              81

<210> SEQ ID NO 20
<211> LENGTH: 627
<212> TYPE: DNA
<213> ORGANISM: Artificial Sequence
<220> FEATURE:
<223> OTHER INFORMATION: synthesized

<400> SEQUENCE: 20
atgaagatgg aggagctgtt taagaagcac aagatcgtgg ccgtgctgag ggccaactcc    60
gtggaggagg ccatcgagaa ggcagtggcc gtgttcgcag gaggagtgca cctgatcgag   120
atcaccttca ccgtgccaga cgccgatacc gtgatcaagg ccctgtccgt gctgaaggag   180
aagggagcaa tcatcggagc aggaacagtg acctctgtgg agcagtgcag gaaggcagtg   240
gagtctggag ccgagttcat cgtgagccct cacctggacg aggagatcag ccagttctgt   300
aaggagaagg gcgtgtttta catgcccggc gtgatgacac taccgagct ggtgaaggcc    360 atgaagctgg ccacgatat cctgaagctg ttcccaggag aggtggtggg acctcagttt    420
gtgaaggcca tgaagggccc tttcccaaac gtgaagtttg tgcccacagg cggcgtgaac   480
ctggacaacg tgtgcgagtg gttcaaggca ggcgtgctgg cagtgggagt gggcgatgcc   540
ctggtgaagg gcgaccctga tgaggtgcgc gagaaggcca gaagtttgt ggagaagatc    600 agggatgta ccgagggcag cctggag                                       627

<210> SEQ ID NO 21
<211> LENGTH: 72
<212> TYPE: DNA
<213> ORGANISM: Artificial Sequence

```
<220> FEATURE:
<223> OTHER INFORMATION: synthesized

<400> SEQUENCE: 21
atgccaatgg gctctctgca gcccctggcc acactgtacc tgctgggaat gctggtggca    60
agctgcctgg ga                                                        72

<210> SEQ ID NO 22
<211> LENGTH: 24
<212> TYPE: DNA
<213> ORGANISM: Artificial Sequence
<220> FEATURE:
<223> OTHER INFORMATION: synthesized

<400> SEQUENCE: 22
catcatcacc accaccacca ccac                                           24

<210> SEQ ID NO 23
<211> LENGTH: 483
<212> TYPE: DNA
<213> ORGANISM: Artificial Sequence
<220> FEATURE:
<223> OTHER INFORMATION: synthesized

<400> SEQUENCE: 23
atgaaccagc acagccacaa ggaccacgag accgtgcgta ttgcggtggt tcgtgcgcgt    60
tggcatgcgg agattgtgga tgcgtgcgtt agcgcgttcg aagcggcgat gcgtgacatc   120
ggtggcgatc gtttcgcggt ggacgttttt gatgtgccgg gtgcgtacga gattccgctg   180
catgcgcgta ccctggcgga aaccggtcgt tatggcgcgg ttctgggcac cgcgttcgtg   240
gttaacggtg gcatctaccg tcacgaattt gtggcgagcg cggttattaa cggtatgatg   300
aacgtgcaac tgaacaccgg cgtgccggtt ctgagcgcgg ttctgacccc gcacaactat   360
gacaagagca agcgcacac cctgctgttc ctggcgctgt ttgcggtgaa gggtatggaa   420
gcggcgcgtg cgtgcgttga gatcctggcg gcgcgtgaaa aaattgcggc gggcagcctg   480
gaa                                                                 483

<210> SEQ ID NO 24
<211> LENGTH: 18
<212> TYPE: DNA
<213> ORGANISM: Artificial Sequence
<220> FEATURE:
<223> OTHER INFORMATION: synthesized

<400> SEQUENCE: 24
catcatcacc accaccac                                                  18

<210> SEQ ID NO 25
<211> LENGTH: 24
<212> TYPE: PRT
<213> ORGANISM: Artificial Sequence
<220> FEATURE:
<223> OTHER INFORMATION: synthesized

<400> SEQUENCE: 25

Met Pro Met Gly Ser Leu Gln Pro Leu Ala Thr Leu Tyr Leu Leu Gly
 1               5                  10                  15

Met Leu Val Ala Ser Cys Leu Gly
             20

<210> SEQ ID NO 26
```

```
<211> LENGTH: 12
<212> TYPE: DNA
<213> ORGANISM: Artificial Sequence
<220> FEATURE:
<223> OTHER INFORMATION: synthesized

<400> SEQUENCE: 26
caccaccacc ac                                                         12

<210> SEQ ID NO 27
<211> LENGTH: 2844
<212> TYPE: DNA
<213> ORGANISM: Artificial Sequence
<220> FEATURE:
<223> OTHER INFORMATION: synthesized

<400> SEQUENCE: 27
atgccaatgg gctctctgca gcccctggcc acactgtacc tgctgggaat gctggtggca        60
agctgcctgg gacagacccc agagcagcct gcaccacctg ccaccacagt gcagcctaca       120
gccaccagac agcagaccag cttccccttc cgggtgtgcg agctgagctc ccacggcgac       180
ctgttcagat ttctagcga tatccagtgt ccctccttcg cacaaggga gaaccacacc        240 gagggcctgc tgatggtgtt caaggacaat atcatccctt actcctttaa ggtgagatct       300
tatacaaaga tcgtgaccaa catcctgatc tacaatggcc acagagccga ttctgtgacc       360
aacaggcacg aggagaagtt tagcgtggag tcctatgaga cagaccagat ggataccatc       420
taccagtgct ataatgccgt gaagatgaca aaggacggcc tgaccagagt gtacgtggac       480
agggatggcg tgaacatcac agtgaatctg aagcctaccg aggactggc aaacggcgtg       540 cggagatacg ccagccagac cgagctgtat gatgcaccag aagggtgga ggcaacatac       600 aggaccagga ccacagtgaa ctgtctgatc acagacatga tggccaagag caattcccca       660
ttcgatttct tgtgaccac aaccggccag accgtggaga tgagccccctt ttatgacggc       720 aagaacacag agaccttcca cgagcgcgcc gattcctttc acgtgcggac aaattacaag       780
atcgtggact atgataacag aggaaccaat ccacagggag agaggagggc cttcctggac       840
aagggcacat acccctgtc ctggaagctg gagaacagga cagcctattg ccccctgcag       900
cactggcaga catttgactc caccatcgcc acagagaccg gcaagtctat ccacttcgtg       960
acagatgagg gcacctcctc tttttgtgacc aacacaaccg tgggcatcga gctgcccgac      1020
gccttcaagt gtatcgagga gcaagtgaat aagacaatgc acgagaagta cgaggccgtg      1080
caggatcgct ataccaaggg ccaggaagcc atcacatact ttatcaccag cggaggactg      1140
ctgctggcat ggctgccact gacaccacgg tccctggcca cagtgaagaa tctgaccgag      1200
ctgacaaccc caaccagctc cccaccatct agcccaagcc ctccagcacc acctgcagca      1260
cggggctcta ccagcgccgc cgtgctgcgg agaaggcgcc ggaacgcagg aaatgcaaca      1320
acccctgtgc caccagcagc acctggcaag tctctgggca cactgaacaa tcccgccacc      1380
gtgcagatcc agttcgccta cgacagcctg agaaggcaga tcaacagaat gctgggcgat      1440
ctggcaaggg catggtgcct ggagcagaag cgccagaaca tggtgctgcg ggagctgacc      1500
aagatcaatc ctacaaccgt gatgtcctct atctatggca aggcagtggc agcaaagaga      1560
ctgggcgacg tgatctccgt gtctcagtgc gtgccagtga atcaggccac agtgaccctg      1620
agaaagagca tgagggtgcc cggctccgag accatgtgct actctaggcc tctggtgagc      1680 ttctcccttta tcaacgacac aaaagaccta tgagggcagc tggcacagaa taatgagatc      1740
ttcctgacaa agaagatgac cgaggtgtgc caggccacca gccagtacta tttccagtcc      1800
```

```
ggcaacgaga tccacgtgta caatgactat caccacttta agacaatcga gctggatggc   1860
atcgccacac tgcagacctt catctctctg aacaccagcc tgatcgagaa tatcgacttt   1920
gccagcctgg agctgtactc cagggacgag cagagggcat ccaacgtgtt cgatctggag   1980
ggcatcttcc gcgagtataa ctttcaggcc cagaatatcg ccggcctgcg gaaggacctg   2040
gataatgccg tgtctggagg aggaggaagc ggaggaggag atccggcgg cggcggctct    2100 ggatacatcc ctgaggcacc aagggacgga caggcctatg tgcggaagga tggcgagtgg   2160
gtgctgctgt ccaccttcct gggctctggc agccatcatc accaccacca ccaccacatg   2220
aagatggagg agctgtttaa gaagcacaag atcgtggccg tgctgagggc caactccgtg   2280
gaggaggcca tcgagaaggc agtggccgtg ttcgcaggag gagtgcacct gatcgagatc   2340
accttcaccg tgccagacgc cgataccgtg atcaaggccc tgtccgtgct gaaggagaag   2400
ggagcaatca tcggagcagg aacagtgacc tctgtggagc agtgcaggaa ggcagtggag   2460
tctggagccg agttcatcgt gagccctcac ctggacgagg agatcagcca gttctgtaag   2520
gagaagggcg tgttttacat gcccggcgtg atgacaccta ccgagctggt gaaggccatg   2580
aagctgggcc acgatatcct gaagctgttc ccaggagagg tggtgggacc tcagtttgtg   2640
aaggccatga agggcccttt cccaaacgtg aagtttgtgc ccacaggcgg cgtgaacctg   2700
gacaacgtgt gcgagtggtt caaggcaggc gtgctggcag tgggagtggg cgatgccctg   2760
gtgaagggcg accctgatga ggtgcgcgag aaggccaaga gtttgtgga aagatcagg    2820 ggatgtaccg agggcagcct ggag                                         2844

<210> SEQ ID NO 28
<211> LENGTH: 948
<212> TYPE: PRT
<213> ORGANISM: Artificial Sequence
<220> FEATURE:
<223> OTHER INFORMATION: synthesized

<400> SEQUENCE: 28

Met Pro Met Gly Ser Leu Gln Pro Leu Ala Thr Leu Tyr Leu Leu Gly
1               5                   10                  15

Met Leu Val Ala Ser Cys Leu Gly Gln Thr Pro Glu Gln Pro Ala Pro
            20                  25                  30

Pro Ala Thr Thr Val Gln Pro Thr Ala Thr Arg Gln Gln Thr Ser Phe
        35                  40                  45

Pro Phe Arg Val Cys Glu Leu Ser Ser His Gly Asp Leu Phe Arg Phe
    50                  55                  60

Ser Ser Asp Ile Gln Cys Pro Ser Phe Gly Thr Arg Glu Asn His Thr
65                  70                  75                  80

Glu Gly Leu Leu Met Val Phe Lys Asp Asn Ile Ile Pro Tyr Ser Phe
                85                  90                  95

Lys Val Arg Ser Tyr Thr Lys Ile Val Thr Asn Ile Leu Ile Tyr Asn
            100                 105                 110

Gly His Arg Ala Asp Ser Val Thr Asn Arg His Glu Glu Lys Phe Ser
        115                 120                 125

Val Glu Ser Tyr Glu Thr Asp Gln Met Asp Thr Ile Tyr Gln Cys Tyr
    130                 135                 140

Asn Ala Val Lys Met Thr Lys Asp Gly Leu Thr Arg Val Tyr Val Asp
145                 150                 155                 160

Arg Asp Gly Val Asn Ile Thr Val Asn Leu Lys Pro Thr Gly Gly Leu
                165                 170                 175
```

```
Ala Asn Gly Val Arg Arg Tyr Ala Ser Gln Thr Glu Leu Tyr Asp Ala
            180                 185                 190

Pro Gly Arg Val Glu Ala Thr Tyr Arg Thr Arg Thr Thr Val Asn Cys
        195                 200                 205

Leu Ile Thr Asp Met Met Ala Lys Ser Asn Ser Pro Phe Asp Phe Phe
210                 215                 220

Val Thr Thr Thr Gly Gln Thr Val Glu Met Ser Pro Phe Tyr Asp Gly
225                 230                 235                 240

Lys Asn Thr Glu Thr Phe His Glu Arg Ala Asp Ser Phe His Val Arg
                245                 250                 255

Thr Asn Tyr Lys Ile Val Asp Tyr Asp Asn Arg Gly Thr Asn Pro Gln
            260                 265                 270

Gly Glu Arg Arg Ala Phe Leu Asp Lys Gly Thr Tyr Thr Leu Ser Trp
        275                 280                 285

Lys Leu Glu Asn Arg Thr Ala Tyr Cys Pro Leu Gln His Trp Gln Thr
290                 295                 300

Phe Asp Ser Thr Ile Ala Thr Glu Thr Gly Lys Ser Ile His Phe Val
305                 310                 315                 320

Thr Asp Glu Gly Thr Ser Ser Phe Val Thr Asn Thr Val Gly Ile
                325                 330                 335

Glu Leu Pro Asp Ala Phe Lys Cys Ile Glu Glu Gln Val Asn Lys Thr
            340                 345                 350

Met His Glu Lys Tyr Glu Ala Val Gln Asp Arg Tyr Thr Lys Gly Gln
        355                 360                 365

Glu Ala Ile Thr Tyr Phe Ile Thr Ser Gly Gly Leu Leu Leu Ala Trp
370                 375                 380

Leu Pro Leu Thr Pro Arg Ser Leu Ala Thr Val Lys Asn Leu Thr Glu
385                 390                 395                 400

Leu Thr Thr Pro Thr Ser Ser Pro Ser Ser Pro Ser Pro Pro Ala
                405                 410                 415

Pro Pro Ala Ala Arg Gly Ser Thr Ser Ala Ala Val Leu Arg Arg Arg
            420                 425                 430

Arg Arg Asn Ala Gly Asn Ala Thr Thr Pro Val Pro Ala Ala Pro
        435                 440                 445

Gly Lys Ser Leu Gly Thr Leu Asn Asn Pro Ala Thr Val Gln Ile Gln
450                 455                 460

Phe Ala Tyr Asp Ser Leu Arg Arg Gln Ile Asn Arg Met Leu Gly Asp
465                 470                 475                 480

Leu Ala Arg Ala Trp Cys Leu Glu Gln Lys Arg Gln Asn Met Val Leu
                485                 490                 495

Arg Glu Leu Thr Lys Ile Asn Pro Thr Thr Val Met Ser Ser Ile Tyr
            500                 505                 510

Gly Lys Ala Val Ala Lys Arg Leu Gly Asp Val Ile Ser Val Ser
        515                 520                 525

Gln Cys Val Pro Val Asn Gln Ala Thr Val Thr Leu Arg Lys Ser Met
530                 535                 540

Arg Val Pro Gly Ser Glu Thr Met Cys Tyr Ser Arg Pro Leu Val Ser
545                 550                 555                 560

Phe Ser Phe Ile Asn Asp Thr Lys Thr Tyr Glu Gly Gln Leu Gly Thr
                565                 570                 575

Asp Asn Glu Ile Phe Leu Thr Lys Lys Met Thr Glu Val Cys Gln Ala
            580                 585                 590
```

Thr Ser Gln Tyr Tyr Phe Gln Ser Gly Asn Glu Ile His Val Tyr Asn
            595                 600                 605

Asp Tyr His His Phe Lys Thr Ile Glu Leu Asp Gly Ile Ala Thr Leu
610                 615                 620

Gln Thr Phe Ile Ser Leu Asn Thr Ser Leu Ile Glu Asn Ile Asp Phe
625                 630                 635                 640

Ala Ser Leu Glu Leu Tyr Ser Arg Asp Glu Gln Arg Ala Ser Asn Val
                645                 650                 655

Phe Asp Leu Glu Gly Ile Phe Arg Glu Tyr Asn Phe Gln Ala Gln Asn
            660                 665                 670

Ile Ala Gly Leu Arg Lys Asp Leu Asp Asn Ala Val Ser Gly Gly Gly
        675                 680                 685

Gly Ser Gly Gly Gly Ser Gly Gly Gly Ser Gly Tyr Ile Pro
    690                 695                 700

Glu Ala Pro Arg Asp Gly Gln Ala Tyr Val Arg Lys Asp Gly Glu Trp
705                 710                 715                 720

Val Leu Leu Ser Thr Phe Leu Gly Ser Gly Ser His His His His
                725                 730                 735

His His His Met Lys Met Glu Glu Leu Phe Lys Lys His Lys Ile Val
            740                 745                 750

Ala Val Leu Arg Ala Asn Ser Val Glu Glu Ala Ile Glu Lys Ala Val
        755                 760                 765

Ala Val Phe Ala Gly Gly Val His Leu Ile Glu Ile Thr Phe Thr Val
    770                 775                 780

Pro Asp Ala Asp Thr Val Ile Lys Ala Leu Ser Val Leu Lys Glu Lys
785                 790                 795                 800

Gly Ala Ile Ile Gly Ala Gly Thr Val Thr Ser Val Glu Gln Cys Arg
                805                 810                 815

Lys Ala Val Glu Ser Gly Ala Glu Phe Ile Val Ser Pro His Leu Asp
            820                 825                 830

Glu Glu Ile Ser Gln Phe Cys Lys Glu Lys Gly Val Phe Tyr Met Pro
        835                 840                 845

Gly Val Met Thr Pro Thr Glu Leu Val Lys Ala Met Lys Leu Gly His
    850                 855                 860

Asp Ile Leu Lys Leu Phe Pro Gly Glu Val Val Gly Pro Gln Phe Val
865                 870                 875                 880

Lys Ala Met Lys Gly Pro Phe Pro Asn Val Lys Phe Val Pro Thr Gly
                885                 890                 895

Gly Val Asn Leu Asp Asn Val Cys Glu Trp Phe Lys Ala Gly Val Leu
            900                 905                 910

Ala Val Gly Val Gly Asp Ala Leu Val Lys Gly Asp Pro Asp Glu Val
        915                 920                 925

Arg Glu Lys Ala Lys Lys Phe Val Glu Lys Ile Arg Gly Cys Thr Glu
    930                 935                 940

Gly Ser Leu Glu
945

<210> SEQ ID NO 29
<211> LENGTH: 167
<212> TYPE: PRT
<213> ORGANISM: Artificial Sequence
<220> FEATURE:
<223> OTHER INFORMATION: synthesized

<400> SEQUENCE: 29

```
Met Asn Gln His Ser His Lys Asp His Glu Thr Val Arg Ile Ala Val
1               5                   10                  15
Val Arg Ala Arg Trp His Ala Glu Ile Val Asp Ala Cys Val Ser Ala
                20                  25                  30
Phe Glu Ala Ala Met Arg Asp Ile Gly Gly Asp Arg Phe Ala Val Asp
            35                  40                  45
Val Phe Asp Val Pro Gly Ala Tyr Glu Ile Pro Leu His Ala Arg Thr
        50                  55                  60
Leu Ala Glu Thr Gly Arg Tyr Gly Ala Val Leu Gly Thr Ala Phe Val
65                  70                  75                  80
Val Asn Gly Gly Ile Tyr Arg His Glu Phe Val Ala Ser Ala Val Ile
                85                  90                  95
Asn Gly Met Met Asn Val Gln Leu Asn Thr Gly Val Pro Val Leu Ser
            100                 105                 110
Ala Val Leu Thr Pro His Asn Tyr Asp Lys Ser Lys Ala His Thr Leu
            115                 120                 125
Leu Phe Leu Ala Leu Phe Ala Val Lys Gly Met Glu Ala Ala Arg Ala
            130                 135                 140
Cys Val Glu Ile Leu Ala Ala Arg Glu Lys Ile Ala Ala Gly Ser Leu
145                 150                 155                 160
Glu His His His His His His
                165
```

SELF-ASSEMBLED NANOPARTICLE CONTAINING GB PROTEIN OF EB VIRUS AND PREPARATION METHOD AND USE THEREOF

CROSS-REFERENCE TO RELATED APPLICATIONS

The present application is a national phase entry under 35 USC § 371 of International Application PCT/CN2020/136752, filed Dec. 16, 2020, which claims the benefit of and priority to Chinese Patent Application No. 2020114170910, filed Dec. 7, 2020, the entire disclosures of which are incorporated herein by reference.

TECHNICAL FIELD

The present disclosure belongs to the field of biotechnology, and more particularly, relates to a self-assembled nanoparticle containing a gB protein of an EB virus and a preparation method and use thereof.

BACKGROUND

An Epstein-Barr Virus (EBV) belongs to a herpes virus family. EBV has a latent infection ability and is one of the earliest identified carcinogenic viruses. EBV infects 95% of the population in the world, and mainly causes infectious mononucleosis in adolescents. Moreover, EBV is closely related to epithelial tumors such as nasopharyngeal carcinoma and gastric cancer, and B-cell tumors such as Burkitt lymphoma and Hodgkin lymphoma in adults. Therefore, it is of great public health significance to develop EBV vaccines.

As an enveloped virus, EBV infects host cells by membrane fusion. This process is completed by an interaction between membrane fusion proteins gB, gH/gL, gp42, and the like on the surface of EBV and a host cell receptor. At present, it has been found that neutralizing antibodies of these membrane fusion proteins can inhibit EBV from infecting epithelial cells or B cells, therefore, these major membrane fusion proteins are ideal candidate antigens for developing EBV vaccines. As the co-executive proteins during the membrane fusion, gH-gL and gB work together to promote the fusion of EBV. At present, receptor binding proteins such as gp350 and gH-gL are used as targets in almost all EBV vaccines, and gB is rarely used as an immunogen. Compared with gH-gL and other proteins, gB with a trimerization conformation has a more complex structure and more diverse functions, so that it is more unknown and challenging to develop vaccines with gB as an immunogen.

SUMMARY

In order to overcome the defects in the prior art, an objective of a first aspect of the present disclosure is to provide a self-assembled nanoparticle containing a gB protein.

An objective of a second aspect of the present disclosure is to provide a preparation method of the self-assembled nanoparticle containing the gB protein.

An objective of a third aspect of the present disclosure is to provide use of the self-assembled nanoparticle in the preparation of a drug for preventing EB virus infection.

An objective of a fourth aspect of the present disclosure is to provide a vaccine comprising the self-assembled nanoparticle.

An objective of a fifth aspect the present disclosure is to provide use of the self-assembled nanoparticle in the preparation of a drug for treating diseases caused by EB virus infection.

In order to achieve the objectives above, the technical solutions used in the present disclosure are as follows.

In the first aspect of the present disclosure, a self-assembled nanoparticle containing a gB protein is provided, which comprises a first polypeptide and a second polypeptide, wherein the first polypeptide comprises a gB protein and a first vector subunit, the second polypeptide comprises a second vector subunit; the first vector subunit is I53-50A1, the second vector subunit is I53-50B.4PT1; and the gB protein is linked to the first vector subunit through a linker peptide, so that the gB protein is displayed outside the assembled nanoparticle, and an immune response of a body is better stimulated.

Preferably, the first vector subunit and the second vector subunit are self-assembled to form a nanostructure by a noncovalent interaction, the first vector subunit is coated on a surface of the second vector subunit, and the gB protein is displayed on a surface of the nanostructure.

An amino acid sequence of the I53-50A1 is shown in SEQ ID NO: 1.

An amino acid sequence of the I53-50B.4PT1 is shown in SEQ ID NO: 2.

An amino acid sequence of the gB protein is shown in SEQ ID NO: 3.

The linker peptide is a polypeptide containing 5 amino acids to 20 amino acids; and preferably, the linker peptide is a polypeptide containing 10 amino acids to 15 amino acids. More preferably, the linker peptide is a polypeptide with an amino acid sequence shown in any one of SEQ ID NO: 4 to SEQ ID NO: 9; and most preferably, the linker peptide is a polypeptide with an amino acid sequence shown in SEQ ID NO: 9. The linker peptide is used for linking the antigen gB protein to the vector protein, without affecting the immunogenicity of antigen and the correct folding of protein.

Preferably, the first polypeptide further comprises a stable protein.

Preferably, the stable protein is located between the linker peptide and the first vector subunit.

Preferably, the stable protein is a T4 fibritin shown in SEQ ID NO: 10 or a GCN4 peptide fragment shown in SEQ ID NO: 11; and more preferably, the stable protein is the T4 fibritin.

Preferably, the first polypeptide is a first polypeptide trimer.

Preferably, the second polypeptide is a second polypeptide pentamer.

Preferably, the first polypeptide trimer has a copy number ranging from 18 to 22, and the second polypeptide pentamer has a copy number ranging from 10 to 14. More preferably, the first polypeptide trimer has a copy number of 20, and the second polypeptide pentamer has a copy number of 12.

Preferably, the self-assembled nanoparticle containing the gB protein has an icosahedral symmetry.

In the second aspect of the present disclosure, a preparation method of the self-assembled nanoparticle containing the gB protein is provided, comprising the step of incubating the first polypeptide and the second polypeptide to obtain the self-assembled nanoparticle containing the gB protein. The first polypeptide comprises a gB protein and a first vector subunit, and the second polypeptide comprises a second vector subunit; the first vector subunit is I53-50A1, and the second vector subunit is I53-50B.4PT1; and the gB protein is linked to the first vector subunit through a linker peptide, so that the gB protein is displayed outside the assembled nanoparticle, and an immune response of a body is better stimulated.

An amino acid sequence of the I53-50A1 is shown in SEQ ID NO: 1.

An amino acid sequence of the I53-50B.4PT1 is shown in SEQ ID NO: 2.

A molar mass ratio of the first polypeptide to the second polypeptide is preferably 1:3 to 6; and is more preferably 1:5.

The incubation is preferably carried out in an assembled buffer for 0.5 hour to 2 hours.

Preferably, the assembled buffer comprises 250 mm NaCl, 50 mm Tris-HCl with pH 8.0 and 5% glycerol.

An amino acid sequence of the gB protein is shown in SEQ ID NO: 3.

The linker peptide is a polypeptide containing 5 amino acids to 20 amino acids; and preferably, the linker peptide is a polypeptide containing 10 amino acids to 15 amino acids. More preferably, the linker peptide is a polypeptide with an amino acid sequence shown in any one of SEQ ID NO: 4 to SEQ ID NO: 9; and most preferably, the linker peptide is a polypeptide with an amino acid sequence shown in SEQ ID NO: 9. The linker peptide is used for linking the antigen gB protein to a vector protein, without affecting the immunogenicity of antigen and the correct folding of protein.

Preferably, the first polypeptide further comprises a stable protein.

Preferably, the stable protein is located between the linker peptide and the first vector subunit.

The stable protein is preferably a T4 fibritin shown in SEQ ID NO: 10 or a GCN4 peptide fragment shown in SEQ ID NO: 11; and more preferably, the stable protein is the T4 fibritin.

Preferably, the first polypeptide and the second polypeptide further comprise a purification tag.

Preferably, the purification tag is at least one selected from the group consisting of histidine tag (His tag), streptavidin tag (Strep tag) and maltose binding protein (MBP); and more preferably, the purification tag is the histidine tag (His tag).

The purification tag of the first polypeptide is located between the stable protein and the first vector subunit.

The purification tag of the second polypeptide is located at a tail end of the second vector subunit.

The first polypeptide further comprises a signal peptide, so that a target protein can be secreted to a supernatant after expression.

The signal peptide is a CD5 signal peptide shown in SEQ ID NO: 25.

Preferably, the first polypeptide is obtained by the following steps: introducing a nucleic acid expressing the first polypeptide into a first host cell; and incubating the first host cell to express the first polypeptide.

Preferably, the first host cell is a eukaryotic cell; more preferably, the first host cell is at least one selected from the group consisting of human embryonic kidney 293 cell (HEK293F), Madin-Daby canine kidney cell (MDCK), Chlorocebus sabaeus kidney cell (VERO), SF9 (*Spodoptera frugiperda* 9) cell, HighFive cell, CHO (Chinese Hamster Ovary) cell, and yeast cell; and most preferably, the first host cell is the human embryonic kidney 293 cell.

Preferably, the second polypeptide is obtained by the following steps: introducing a nucleic acid expressing the second polypeptide into a second host cell; and incubating the second host cell to express the second polypeptide.

Preferably, the second host cell is a prokaryotic cell; more preferably, the second host cell is *Escherichia coli*; and most preferably, the second host cell is Rosetta(DE3).

In the third aspect of the present disclosure, use of the self-assembled nanoparticle in the first aspect in the preparation of a drug for preventing EB virus infection is provided.

In the fourth aspect of the present disclosure, a vaccine comprising the self-assembled nanoparticle in the first aspect is provided.

A vaccine comprising the self-assembled nanoparticle containing the gB protein is provided.

The vaccine further includes an adjuvant.

Preferably, the adjuvant is at least one selected from the group consisting of an aluminum adjuvant, an oil emulsion adjuvant such as oil-in-water emulsion, water-in-oil emulsion and bidirectional emulsion, a microorganism-originated adjuvant such as peptidoglycan (PG), lipopolysccharide (LPS) of Gram-negative bacterial outer membrane, mycobacteria and components thereof, GpG oligonucleotide (GpG ODN) and cholera toxin (CT), a microsomal antigen delivery system such as liposome, polymeric microsphere, inert nanosphere, nano aluminum adjuvant, immunostimulating complex (IS-COM), cytokine, a polysaccharide such as inulin (MPI), and a natural source such as propolis and sapoin. More preferably, the adjuvant is at least one selected from the group consisting of aluminum adjuvant and MF59 adjuvant.

In the fifth aspect of the present disclosure, use of the self-assembled nanoparticle in the first aspect in the preparation of a drug for treating diseases caused by EB virus infection is provided.

Preferably, the disease is at least one selected from the group consisting of infectious disease, malignant tumor, chronic disease and autoimmune disease. More preferably, the disease is at least one selected from the group consisting of mononucleosis, nasopharyngeal carcinoma, gastric carcinoma, epithelial tumor, Burkitt lymphoma, Hodgkin lymphoma, chronic fatigue syndrome, multiple sclerosis and ankylosing myelitis.

The drug further comprises a pharmaceutically acceptable carrier.

The present disclosure has the beneficial effects as follows:

In the self-assembled nanoparticle provided herein, the gB protein of the EB virus is displayed on the surface of the nanoparticle for the first time. The particle size of the self-assembled nanoparticle is larger than that of the antigen (gB), the heat stability of the self-assembled nanoparticle is equivalent to that of the antigen (gB), the chemical stability of the self-assembled nanoparticle is higher than that of the antigen (gB), and the binding capacity with the neutralizing antibody of the self-assembled nanoparticle is higher than that of the antigen (gB), which are beneficial for prolonging residence time of the self-assembled nanoparticle in the B cell antigen receptor and stimulating generation of the antibody. Meanwhile, the self-assembled nanoparticle is capable of inducing a higher animal immune antibody titer, and is suitable for preventing EB virus infection and treating diseases caused by EB virus infection.

Although a heterologous gene is introduced into the self-assembled nanoparticle provided herein, since the heterologous gene is derived from the protein of bacteria, which can avoid causing autoimmune diseases, thus having an advantage of high safety without affecting an immune effect.

BRIEF DESCRIPTION OF DRAWINGS

FIG. 1A is a schematic diagram of docking the gB antigen with the nanoparticle skeleton protein I53-50A1, and the self-assembled nanoparticle formed; and FIG. 1B is a schematic diagram of docking the gB antigen with different nanoparticle skeleton proteins.

FIG. 7A is a result diagram of differential fluorescence scanning, which shows a change of a ratio of F330 to F350 of the protein of the self-assembled nanoparticle during heating; FIG. 7B is a result diagram of differential fluorescence scanning, which shows a first-order derivative value of the change of the ratio of F330 to F350 of the protein of the self-assembled nanoparticle during heating;

and FIG. 7C is a result diagram of differential fluorescence scanning, which shows a change of scattered light of the protein of the self-assembled nanoparticle during heating.

FIG. 8 is a diagram of Tm onset and Tm of the self-assembled nanoparticle, wherein Tm onset is a temperature at which melting begins, and Tm is a melting temperature.

FIG. 9A is a diagram showing the change of the ratio of F330 to F350 of the protein of nanoparticle vector (I53-50A NP) under different concentrations of guanidine hydrochloride during heating; FIG. 9B is a diagram showing the change of the ratio of F330 to F350 of the protein of gB under different concentrations of guanidine hydrochloride during heating; FIG. 9C is a diagram showing the change of the ratio of F330 to F350 of the protein of self-assembled nanoparticle (gB-I53-50A NP) under different concentrations of guanidine hydrochloride during heating; FIG. 9D is a diagram showing the change of scattered light of the protein of the nanoparticle vector (I53-50A NP) under different concentrations of guanidine hydrochloride during heating; FIG. 9E is a diagram showing the change of scattered light of the protein of gB under different concentrations of guanidine hydrochloride during heating; and FIG. 9F is a diagram showing the change of scattered light of the protein of the self-assembled nanoparticle (gB-I53-50A NP) under different concentrations of guanidine hydrochloride during heating.

FIG. 10A is a diagram of a binding point between gB and an AMMO5 antibody; FIG. 10B is a diagram of a binding point between a subunit gB-I53-50A1 and the AMMO5 antibody; and FIG. 10C is a diagram of a binding point between the self-assembled nanoparticle (gB-I53-50A NP) and the AMMO5 antibody.

DETAILED DESCRIPTION

Figure 2:
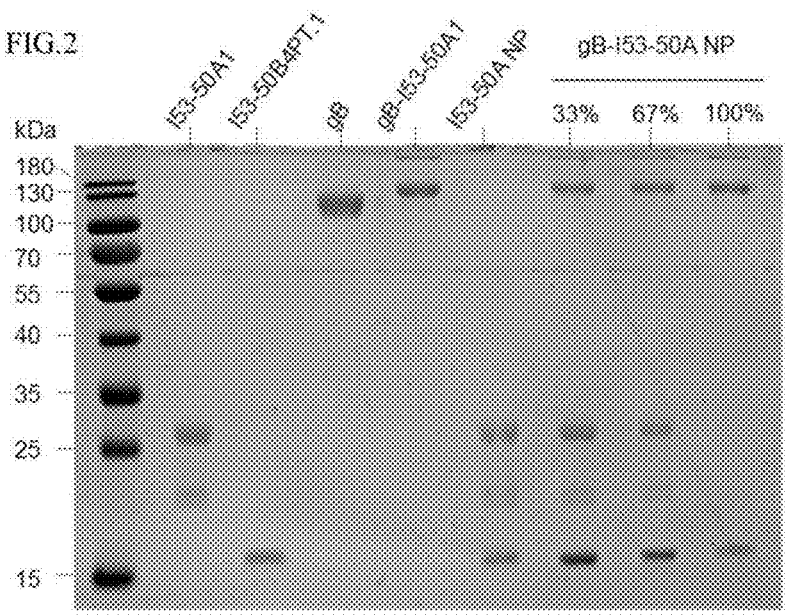
FIG. 2 is a Coomassie brilliant blue staining graph of SDS-PAGE electrophoresis of the self-assembled nanoparticle.

The contents of the present disclosure are further described in detail hereinafter with reference to the specific example and the accompanying drawings.

It should be understood that these examples are only used for describing the present disclosure and are not intended to limit the scope of the present disclosure.

In the following examples, if the specific conditions of the experimental methods are not indicated, the conventional conditions are generally used. Various common chemical reagents used in the examples are all commercially available products.

The preparation method of the nanoparticle vaccine in the present disclosure includes the following steps.

A. An appropriate fusion distance is determined through computer aided designs such as Sic_axle, Rosetta and the like, so as to determine a length of a linker for nanoparticle design in a sequence, and design a corresponding nanoparticle vector based on the length.

B. An appropriate quantity of eukaryotic expression vectors are transferred into a host first cell for expression by a transient transfection technology to obtain a nanoparticle subunit protein (a first polypeptide) of gB-I53-50A1. Meanwhile, the expression plasmid of I53-50B.4PT1 is transformed by using a second host cells, and after induction with IPTG, another nanoparticle subunit protein (a second polypeptide) of I53-50B.4PT1 is expressed and obtained.

C. gB-I53-50A1 and I53-50B.4PT1 subunits are added into an assembling buffer according to a certain proportion, and incubated at a room temperature to obtain an assembled nanoparticle. The assembled nanoparticle is separated by molecular exclusion chromatography, and particle size distribution and stability of the protein is determined by negative staining electron microscopy, dynamic light scattering and differential scanning fluorescence.

D. An antigenicity of the nanoparticle is determined by bio-layer interferometry (BLI).

E. The nanoparticle is evenly mixed with an adjuvant, and a Balb/C mouse is immunized to verify an antibody level against gB generated in the mouse and a neutralizing ability of serum of the mouse to an EBV virus.

The nanoparticle vaccine of the present application is further described in detail hereinafter.

Example 1 Design of Linker and Vector

The appropriate fusion distance between the antigen (gB protein, SEQ ID NO: 3) and the nanoparticle carrier (I53-50) was determined through computer aided designs such as Sic_axle, Rosetta and the like, so as to determine the length of the linker for linking the antigen to the nanoparticle vector in the sequence, and design the corresponding nanoparticle vector based on the length.

The software used in the design were: Sic_axle (Marcandalli et al., 2019, Cell 177, 1420-1431), and Rosetta (Bale et al., 2016, Science 353, 389-394.).

www.rosettacommons.org/docs/latest/scripting_documentation/RosettaScripts/Movers/movers pages/RelaxScript.

The results were shown in FIG. 1A and FIG. 1B. In FIG. 1A, after docking, the distance between C end of gB and N end of the nanoparticle vector subunit is 56.1 A, so that the appropriate length of the linker shall not be shorter than 56.1 A. Linker regions with different lengths are designed (as shown in Table 1), and different vector (I53-50, T3-10, O3-33, T33-15 and T33-31, as shown in Table 2) are selected. The self-assembled nanoparticle expected to be constructed was shown FIG. 1A, and FIG. 1B was a schematic diagram of docking gB with other nanoparticle vector subunits.

After comparing the final docking structure model and the docking distance, since the shortest docking distance could be finally obtained when I53-50 was docked with the antigen gB as the vector, the vector I53-50 was finally selected and served as the appropriate vector for further design. The vector I53-50 comprised subunits I53-50A1 (SEQ ID NO: 1) and I53-50B.4PT1 (SEQ ID NO: 2).

TABLE 1

Sequence of linker

| Sequence No. | Linker |
| --- | --- |
| SEQ ID NO: 4 | GGGGSGGGGS |
| SEQ ID NO: 5 | GGGGSGGGGSG |
| SEQ ID NO: 6 | GGGGSGGGGSGS |
| SEQ ID NO: 7 | GGGGSGGGGSGGS |
| SEQ ID NO: 8 | GGGGSGGGGSGGGS |
| SEQ ID NO: 9 | GGGGSGGGGSGGGGS |

TABLE 2

Information of vectors

| ID | PDB code | Particle property | Docking distance |
| --- | --- | --- | --- |
| T3-10 | 4EGG | Tetrahedron | 56.9 A |
| O3-33 | 3VCD | Octahedron | 52.42 A |
| T33-15 | 4NWO | Co-assembling tetrahedron | 59.82 A |
| T33-31 | 4ZK7 | Co-assembling tetrahedron | 51.54 A |
| I53-50 | 6P6F | Co-assembling icosahedron | 49.5 A |

Example 2 Construction and Protein Expression of Recombinant Vector

1. Experimental Materials (1) Expression vectors: eukaryotic expression vector pcDNA3.1(+) (ThermoFisher), prokaryotic expression vector pET28a(+) (ThermoFisher), and *Escherichia coli* competent cell DH5a (Tiangen).

(2) Expression systems: Eukaryotic expression system cell HEK293F(ATCC) and transformed *Escherichia coli* cell Rosetta (DE3) (Tianen).

(3) Reagents and materials: PCR enzyme (GeneStar), recombinant enzyme (Vazyme), restriction endonuclease (NEB), gel recovery reagent (GeneStar), plasmid midiprep kit (MN), cell transfection reagent PEI (Polyscience), 293F culture medium (Union), TB culture medium (Xiangbo Bio), purified agarose beads of histidine tag protein (Roche), and other conventional reagents and materials purchased commercially.

(4) Genes: gB gene of EB virus (M81 strain) and I53-50A1/I53-50B particle subunit gene optimized based on bacterial protein were optimized and synthesized through the OptimumGene™ codon platform of Nanjing Genscript Biological Co., Ltd . . .

2. Screening of Linker

Expression vector s with different lengths of linkers were constructed for transfection and expression, then the protein concentration was determined after purification and concentration. The specific steps were as follows: (1) The gB gene of the EB virus (SEQ ID NO: 12), the linkers (with a nucleic acid sequence shown in Table 3), T4 fibritin (SEQ ID NO: 19) and I53-50A1 (SEQ ID NO: 20) were inserted into the vector pcDNA3.1(+) by PCR amplification and enzyme digestion recombination, so as to obtain the target gene gB-I53-50A1 expressed by the expression vector. Wherein, the front end of the vector pcDNA3.1(+) was provided with a CD5 signal peptide (SEQ ID NO: 21) for secreting the expressed polypeptide outside cells, the tail end of the T4 fibritin was provided with the histidine tag (SEQ ID NO: 22) of 8 histidines for convenient purification, and the tail end of the histidine tag was linked to a linking sequence (SEQ ID NO: 26). (2) The recombinant vector gene in pcDNA3.1 was transformed into DH5a competent bacteria, and positive clones were screened by ampicillin resistance. Then, the positive clones were picked into a TB culture medium containing 0.1% ampicillin (0.1 mg/mL) for amplification, and then extracted by the midiprep kit. The specific method could be referred to the instruction of product. (3) 293F cells were subjected to suspension culture and amplification in the 293F culture medium (Union), and were ready for transient transfection after being amplified to a certain quantity. The cells were diluted to 1 L with a density of 1*10⁶/mL, and then, the transfection system of 1 mg of pcDNA3.1-target protein vector 5 mg PEI was prepared with a fresh culture medium, added into the diluted 293F cells after standing for 30 minutes, and cultured at 37° C., 80% humidity and 5% $CO_2$ concentration for 7 days under shaking at 120 rpm. The cell precipitate was removed by centrifugation. The supernatant was filtered by the 0.22 μm filter membrane, and then purified by protein affinity chromatography and molecular sieve to obtain a high-purity target protein gB-I53-50A1 subunit. Results were shown in Table 3, which indicated that the gB-I53-50A1 subunit had the highest yield when the linker was GGGGSGGGGSGGGGS (SEQ ID NO: 9).

TABLE 3

Protein yields of vectors with different linkers

| Linker (nucleic acid sequence) | Linker (amino acid sequence) | Length of amino acid sequence | Yield (mg/L culture medium) |
| --- | --- | --- | --- |
| GGAGGAGGAGGAAGCGGAGGAGGAGGAGG ATCC (SEQ ID NO: 13) | GGGGSGGGGS (SEQ ID NO: 4) | 10 | 0.1 |

TABLE 3-continued

Protein yields of vectors with different linkers

| Linker (nucleic acid sequence) | Linker (amino acid sequence) | Length of amino acid sequence | Yield (mg/L culture medium) |
|---|---|---|---|
| GGAGGAGGAGGAAGCGGAGGAGGAGG ATCCGGC (SEQ ID NO: 14) | GGGGSGGGGSG (SEQ ID NO: 5) | 11 | 0.25 |
| GGAGGAGGAGGAAGCGGAGGAGGAGG ATCCGGCGGC (SEQ ID NO: 15) | GGGGSGGGGSGS (SEQ ID NO: 6) | 12 | 0.72 |
| GGAGGAGGAGGAAGCGGAGGAGGAGG ATCCGGCGGCGGC (SEQ ID NO: 16) | GGGGSGGGGSGGS (SEQ ID NO: 7) | 13 | 0.44 |
| GGAGGAGGAGGAAGCGGAGGAGGAGG ATCCGGCGGCGGCGGC (SEQ ID NO: 17) | GGGGSGGGGSGGGS (SEQ ID NO: 8) | 14 | 0.34 |
| GGAGGAGGAGGAAGCGGAGGAGGAGG ATCCGGCGGCGGCGGCTCT (SEQ ID NO: 18) | GGGGSGGGGSGGGGS (SEQ ID NO: 9) | 15 | 1.2 |

3. Preparation Steps of Self-Assembled Nanoparticle (1) The gB gene of the EB virus (SEQ ID NO: 12), the linker (SEQ ID NO: 18), T4 fibritin (SEQ ID NO: 19) and I53-50A1 (SEQ ID NO: 20) were inserted into the vector pcDNA3.1(+) by PCR amplification and enzyme digestion recombination, so as to obtain the target gene gB-I53-50A1 (SEQ ID NO: 27) expressed by the expression vector. The front end of the vector pcDNA3.1(+) was provided with the CD5 signal peptide (SEQ ID NO: 21) for secreting the expressed polypeptide outside cells, the tail end of the T4 fibritin was provided with the histidine tag (SEQ ID NO: 22) of 8 histidines for convenient purification, and the tail end of the histidine tag was linked to a linking sequence (SEQ ID NO: 26). Moreover, I53-50B.4PT1 (SEQ ID NO: 23) was directly inserted into the vector pET28a(+) during synthesis, and the tail end of the vector pET28a(+) was provided with the histidine tag (SEQ ID NO: 24) of 6 histidines for convenient purification. After sequencing and comparison, the successfully constructed vector was selected for the next experiment.

(2) The recombinant vector gene in pcDNA3.1 was transformed into the DH5a competent bacteria, and the positive clones were screened by ampicillin resistance. Then, the positive clones were picked into the TB culture medium containing 0.1% ampicillin (0.1 mg/mL) for amplification, and then extracted by the midiprep kit. The specific method could be referred to the instruction of product.

(3) The recombinant vector gene in pET28a(+) was transformed into Rosetta (DE3) competent bacteria, and positive clones were screened by kanamycin resistance. Then, the positive clones were picked into the TB culture medium containing 0.1% kanamycin (0.03 g/mL) for amplification, and then further amplified to 1 L in a conical flask, and kanamycin and chloramphenicol were added for screening positive cells. 0.2 mM chemical inducer isopropyl thiogalactoside (IPTG) was added at 18° C. to induce expression of the target protein, and after induction for 20 hours, bacterial cells were collected, crushed under a high pressure, and centrifuged to obtain a supernatant. The supernatant was filtered at 0.22 μm, and purified by protein affinity chromatography and molecular sieve to obtain a high-purity target protein I53-50B.4PT1 subunit (SEQ ID NO: 29).

(4) The 293F cells were subjected to suspension culture and amplification in the 293F culture medium (Union), and were ready for transient transfection after being amplified to a certain quantity. The cells were diluted to 1 L with the density of $1*10^6$/mL, and then, the transfection system of 1 mg of pcDNA3.1-target protein vector 5 mg PEI was prepared with the fresh culture medium, added into the diluted 293F cells after standing for 30 minutes, and cultured at 37° C., 80% humidity and 5% $CO_2$ concentration for 7 days under shaking at 120 rpm. The cell precipitate was removed by centrifugation. The supernatant was filtered by the 0.22 μm filter membrane, and then purified by protein affinity chromatography and molecular sieve to obtain the high-purity target protein gB-I53-50A1 subunit (SEQ ID NO: 28).

(5) The two subunits (gB-I53-50A1 and I53-50B.4PT1) were added into the assembling buffer (250 mM NaCl, 50 mM Tris-HCl with pH 8.0, and 5% glycerol) according to the molar ratio of 1:5, and incubated at the room temperature for 1 hour, and then the assembled nanoparticles (gB-I53-50A NP) with 100% display density was separated by using the molecular sieve. The two subunits (gB-I53-50A1 and I53-50B.4PT1) were added into the assembling buffer (250 mm NaCl, 50 mm Tris-HCl with PH 8.0, and 5% glycerol) according to a molar ratio of 1:2, and incubated at the room temperature for 1 hour, and then the assembled nanoparticle (gB-I53-50A NP) with 33% display density was separated by using the molecular sieve. The two subunits (gB-I53-50A1 and I53-50B.4PT1) were added into the assembling buffer (250 mm NaCl, 50 mm Tris-HCl with pH 8.0, and 5% glycerol) according to a molar ratio of 2:1, and incubated at the room temperature for 1 hour, and then the assembled nanoparticle (gB-I53-50A NP) with 67% display density was separated by using the molecular sieve.

4. Results

Figure 3:
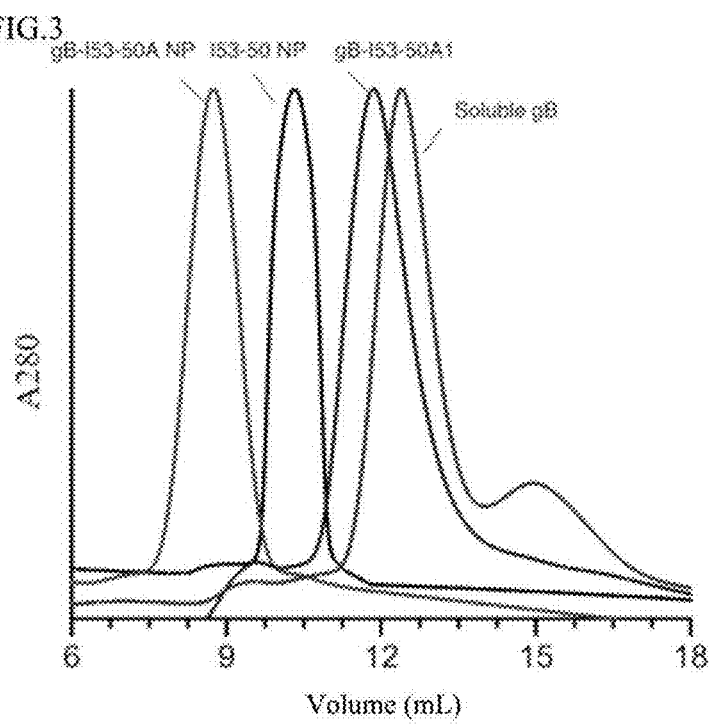
FIG. 3 is a molecular sieve chromatogram of the self-assembled nanoparticle.

As shown in FIG. 2 and FIG. 3, FIG. 2 shows results of Coomassie brilliant blue staining of SDS-PAGE electrophoresis of the nanoparticle: nanovector subunit I53-50A1 (the preparation method of which is the same as the preparation method of the gB-I53-50A1 subunit in the Point 3, except that in step (1), the gB gene of the EB virus, the linker and the T4 fibritin were not inserted into the vector pcDNA3.1 (+)), nanovector subunit I53-50B.4PT1 (the preparation method of which is the same as the preparation method of the I53-50B.4PT1 subunit in Point 3), antigen gB (SEQ ID NO: 3), recombinant nanoparticle gB-I53-50A1 only comprising the nanovector subunit I53-50A1 (the preparation method of which is the same as the preparation method of the gB-I53-50A1 subunit in Point 3), nanoparticle vector I53-50A NP without an antigen (the preparation method of which is the same as the preparation method of the nanoparticle (gB-I53-50A NP) with 100% display density in Point 3, except that in step (1), the gB gene of the EB virus, the linker and the T4 fibritin were not inserted into the vector pcDNA3.1(+)), and recombinant nanoparticle protein gB-I53-50A NP with multiple display densities containing the antigen gB, the I53-50A1 and the I53-50B.4PT1 (the preparation method of which is the same as the preparation method of the nanoparticle (gB-I53-50A NP) with different display densities in Point 3) are shown from left to right. FIG. 3 is a molecular sieve chromatogram of the nanoparticle. It could be seen from FIG. 3 that, the recombinant vector was successfully constructed, and the high-purity nanoparticle protein (gB-I53-50A NP) could be obtained. The molecular mass of gB-I53-50A1 was greater than that of gB, and the size of gB-I53-50A NP after nano granulation is larger than that of the blank particle I53-50 NP, which showed that gB was displayed on the surface of the nanoparticle after assembly.

Figure 4:
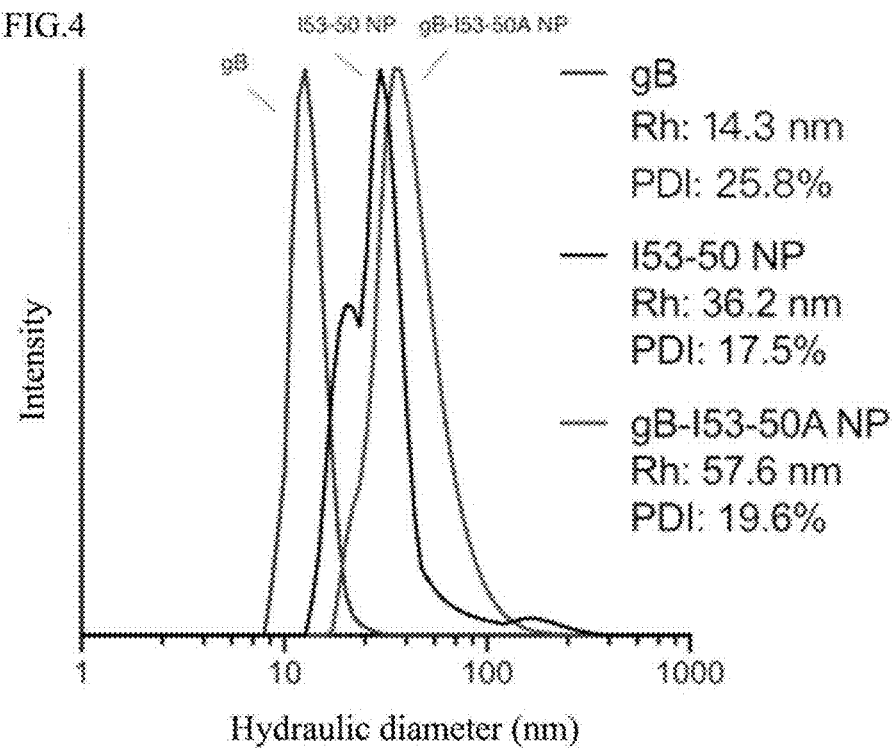
FIG. 4 is a result diagram of dynamic light scattering of the self-assembled nanoparticle.
Figure 5:
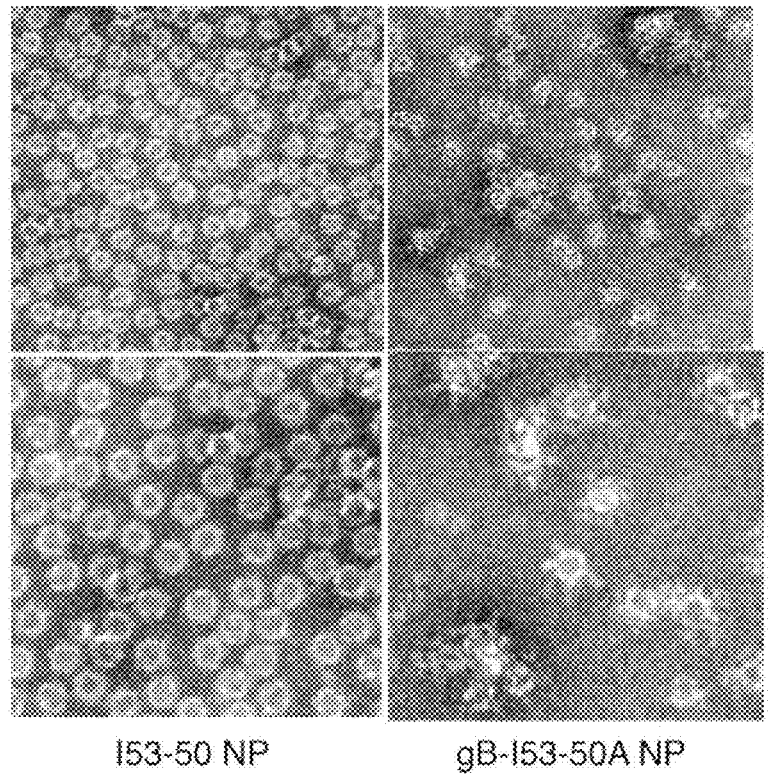
FIG. 5 is a negative staining electron micrograph of the self-assembled nanoparticle.
Figure 6A:
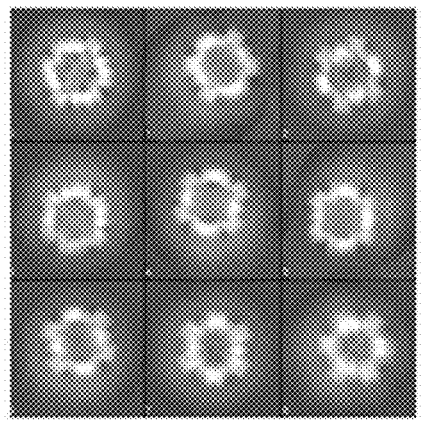
FIG. 6A is a cryo-electron micrograph, which shows the 2D classification of the self-assembled nanoparticle under Relion3.
Figure 6B:
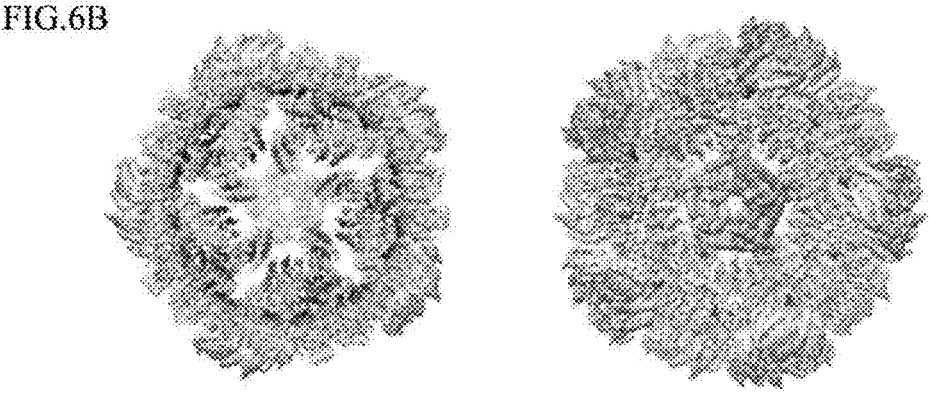
FIG. 6B is a cryo-electron micrograph, which shows the electron density of the self-assembled nanoparticle after reconstruction.
Figure 11A:
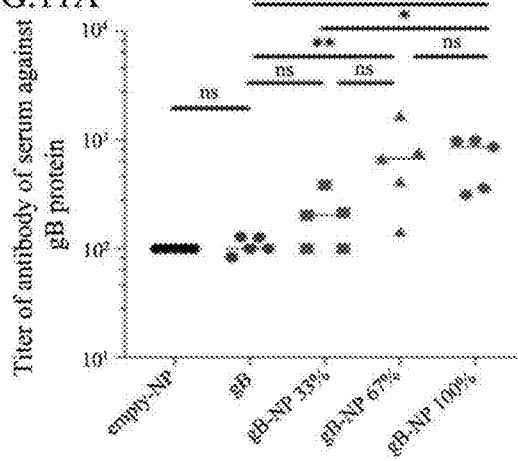
FIG. 11A is a graph of anti-gB serum titers of mice immunized with different particles for two weeks.
Figure 11B:
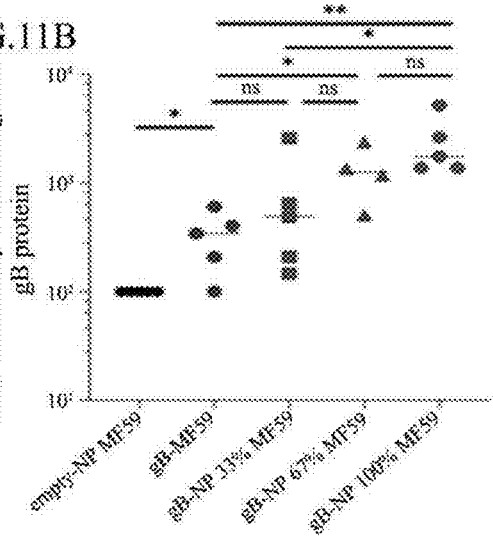
FIG. 11B is a graph of anti-gB serum titers of mice immunized with different particles containing an adjuvant MF59 for two weeks.
Figure 11C:
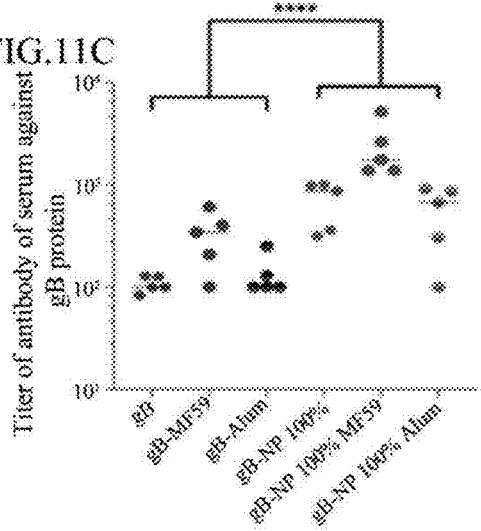
FIG. 11C is a graph of anti-gB serum titers of mice immunized with particles that are added or not added with the nanoparticle vector (I53-50A NP) for two weeks.
Figure 11D:
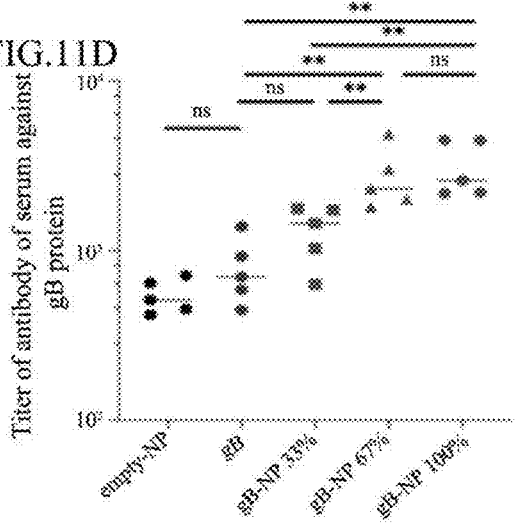
FIG. 11D is a graph of anti-gB serum titers of mice immunized with different particles for five weeks.
Figure 11E:
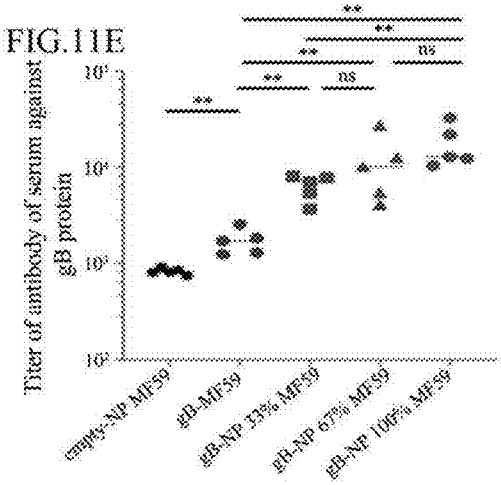
FIG. 11E a graph of anti-gB serum titers of mice immunized with different particles containing the adjuvant MF59 for five weeks.
Figure 11F:
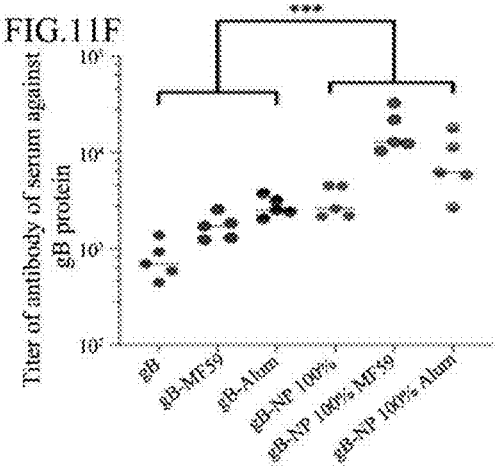
FIG. 11F is a graph of anti-gB serum titers of mice immunized with particles that are added or not added with the nanoparticle vector (I53-50A NP) for five weeks; wherein, * indicates that $P<0.05$;  indicates that $P<0.005$; * indicates that $P<0.0005$; **** indicates that $P<0.00005$; and ns indicates that $P>0.05$.

Example 3 Detection of Structural Characteristic and Chemical Stability of Nanoparticle 1. Experimental Materials
   (1) Unchained Uncle high-throughput protein stability analyzer (Unchained Labs).
   (2) Nano Temper Promethus 48 protein stability analyzer (Nanotemper).
   (3) 120 KV transmission electron microscope (FEI).
   (4) 300 KV cryoelectron microscope (Thermo).
2. Experimental Steps
(1) Detection of Particle Size Distribution of Nanoparticle
   The gB self-assembled nanoparticle (gB-I53-50A NP) with 100% display density in Example 2, the nanoparticle vector (I53-50 NP) and the antigen (gB) were diluted to 0.5 mg/mL. 200 uL of sample was added into a special sample loading slot of Uncle, and stood for 5 minutes, and then the particle size of the nanoparticle was detected by Uncle instrument of Unchained Company.
(2) Detection of Structural Characteristic of Nanoparticle
   The gB self-assembled nanoparticle (gB-I53-50A NP) with 100% display density in Example 2 and the nanoparticle vector (I53-50 NP) were diluted to a concentration ranging from 0.02 mg/mL to 0.2 mg/mL. The protein was incubated on a carbon-coated copper grid, then incubated and stained with 2% uranyl acetate for 2 minutes, and dried in air. Then, the size and morphology of the particle were observed by using the 120 KV transmission electron microscope.
   The gB self-assembled nanoparticle (gB-I53-50A NP) with 100% display density in Example 2 and the nanoparticle vector (I53-50 NP) were diluted to 0.5 mg/mL. The thin-layer cryo-electron microscope sample was prepared by using a sampling machine, and then observed by using the 300 KV cryo-electron microscope, and the structure was built by using Relion3.
(3) Detection of Heat Stability of Nanoparticle
   The gB self-assembled nanoparticle (gB-I53-50A NP) with 100% display density in Example 2, the nanoparticle vector (I53-50 NP), the antigen (gB) and gB-I53-50A1 were diluted to 0.5 mg/ml firs. Then, heating scanning was carried out from 25° C. to 90° C. by using Promethus instrument of Nano Temper Company. Changes of the bifluorescence signal ratio and back reflection aggregation signal were recorded, and the Tm value and aggregation temperature were obtained through the first-order derivative.
(4) Detection of Chemical Stability of Nanoparticle
   The nanoparticle protein was diluted to 0.5 mg/mL first, and then guanidine hydrochloride solutions with the concentration gradient of 0 M to 7 M were added, and incubated overnight at the room temperature. Then, the change of the bifluorescence signal ratio of the protein in different guanidine hydrochloride solutions was detected by using Promethus instrument of Nano Temper Company, and the value of Gibbs free energy change AG was obtained through the first-order derivative.
3. Experimental Results
   As shown in FIG. 4, the gB self-assembled nanoparticle (gB-I53-50A NP) had relatively uniform particle size distribution, and the particle size of the gB self-assembled nanoparticle was significantly larger than that of the nanoparticle vector (I53-50 NP) and that of the antigen (gB), which indicated that gB was successfully displayed on the surface of the particle.
   As shown in FIG. 5, it could be seen that gB-I53-50A NP and I53-50 NP had good homogeneity under negative staining electron microscope, and the surface of the gB-I53-50A NP particle had an obvious external protrusion compared with the I53-50NP empty particle, which indicated that gB was successfully displayed on the surface of the nanoparticle vector.
   As shown in FIG. 6A and FIG. 6B, FIG. 6A is a 2D classification diagram of the nanoparticle under Relion3. It was obvious that the nanoparticle showed regular icosahedron symmetry. FIG. 6B is an electron density map after reconstruction. It could be seen that there were obvious nanoparticles formed by 20 copies of trimer I53-50A1 and 12 copies of pentamer I53-50B4.PT1.
   As shown in FIG. 7A, FIG. 7B, FIG. 7C, and FIG. 8, FIG. 7A to FIG. 7C show results of differential fluorescence scanning of gB, gB-I53-50A1, I53-50 NP and gB-I53-50A NP, wherein FIG. 7A shows the change of the ratio of F330 to F350 of the protein of gB, gB-I53-50A1, I53-50 NP and gB-I53-50A NP during heating; FIG. 7B shows the first-order derivative value of the change of the ratio; and FIG. 7C shows the change of scattered light during heating. It could be seen that the melting temperatures of gB in gB, gB-I53-50A1 and gB-I53-50A NP were almost the same, which proved that granulation had no obvious influence on the structure of gB. In addition, in terms of aggregation information (increase in scattered light), the gB-I53-50A NP particle had no obvious aggregation during heating compared with gB and gB-I53-50A1, which indicated that the heat stability of gB-I53-50A NP particle is better. FIG. 8 shows melting temperature results obtained according to the results of differential fluorescence scanning, wherein Tm onset is the temperature at which melting begins and Tm is the melting temperature. It could be seen that the melting temperatures of gB, gB-I53-50A1 and gB-I53-50A NP were similar, which proved that gB, gB-I53-50A1 and gB-I53-50A NP were highly similar in the heat stability structure, and the structural change did not destroy physical and chemical properties of gB.
   As shown in FIG. 9A to FIG. 9F, the half denaturation concentration of gB was lower than that of gB-I53-50ANP under the guanidine hydrochloride of different concentrations, which mean that the chemical stability of the granulated gB (gB-I53-50A NP) was higher than that of gB. Moreover, the Gibbs free energy of the granulated gB (gB-I53-50A NP) was lower than that of gB, which mean that the nanoparticle (gB-I53-50A NP) not only did not destroy the physical and chemical properties of the antigen gB itself, but also had higher stability than gB on the premise of ensuring the uniformity. In addition, it could be proved that I53-50 NP has the function of stabilizing gB.

Embodiment 4 Antigenicity of Nanoparticle

1. Experimental Materials
   (1) ProteinA sensor (Fortebio), PBS, and Tween 20 (Sigma-Aldrich).
   (2) Fortebio Octet 96 instrument.
   (3) Pre-wetting plate, 96-well plate, and other commercial and conventional consumables.
2. Experimental Steps
   (1) The affinity between the nanoparticle and the neutralizing antibody was detected by using BLI.

0.5% PBST was prepared for kinetic detection. 150 uL of PBST was added into the pre-wetting plate, and incubated in the proteinA sensor for 10 minutes. The antibody AMMO5 (please refer to the document Snijder et al., 2018, Immunity 48, 799-811 for its preparation method) was diluted for coupling. After equilibrium, the coupling was started, and then the antigens such as the protein of the nanoparticle (gB, gB-I53-50A1 and gB-I53-50A NP with 100% display density in Example 2) were diluted in gradient (6.25 nM, 12.5 nM, 25 nM, 50 nM and 100 nM), and bound to the sensor. The binding signal and the dissociation signal were recorded, and the sensor was regenerated by using the glycine solution. The binding signal was fitted by using a binding model of 1:1 to calculate the dynamic parameters.
3. Experimental Results As shown in FIG. 10A to FIG. 10C and Table 4, the gB nanoparticle (gB-I53-50A NP) had a stronger binding ability to the AMMO5 antibody compared to gB, which proved that the antigenicity of the gB nanoparticle is stronger than that of gB. In addition, the gB nanoparticle (gB-I53-50A NP) had a longer dissociation time. Especially, it is almost difficult for the nanoparticle to dissociate from the antibody, which is beneficial for staying on BCR (B cell antigen receptor) for a long time, and stimulating generation of the antibody.

TABLE 4

Kinetic parameters of antibody affinities of gB, gB-I53-50A1 and gB-I53-50A NP

|  | KD (M) | kon (1/Ms) | Kdis (1/s) |
| --- | --- | --- | --- |
| gB | 1.82E−09 | 2.12E+05 | 3.87E−04 |
| gB-I53-50A1 | 1.63E−09 | 1.24E+05 | 2.03E−04 |
| gB-I53-50A NP | 1.24E−09 | 8.95E+05 | 1.11E−04 |

Embodiment 5 Animal Immunogenicity of Protein of Nanoparticle

1. Experimental Materials
   (1) Mice: BalB/C mice, female, 6 weeks to 8 weeks of age (Beijing Charles River Laboratory Animal Technology Co., Ltd.).
   (2) Adjuvant: Inject A aluminum adjuvant (ThermoFisher), and MF59 adjuvant {0.5% (v/v)Tween 80, 0.5% (v/v)Span 85, 4.3% (v/v) squalene, 10 nM sodium citrate buffer}.
   (3) Other commercial and conventional reagent.
2. Experimental Steps
   (1) 0.5 ug of empty nanovector (empty-NP, and I53-50 NP in Example 2), 5 ug of gB protein of EB virus, and particles with 33%, 67% and 100% display densities containing gB of equal molar mass (gB-I53-50A NP in Example 2) were respectively mixed with the above two adjuvants (Inject A aluminum adjuvant and MF59 adjuvant) or respectively diluted with PBST, that was, the adjuvants or PBST was mixed with the antigen according to the mass ratio of 1:1, and incubated under shaking overnight at 4° C. The mice were immunized by subcutaneous immunization.
   (2) The mice were immunized again in the third week after immunization. In the second week and the fifth week after immunization, the orbital blood of the mice was collected, and separated to collect serum. The total antibody titer of gB in the serum of the mice was detected through indirect enzyme-linked immunosorbent assay.
3. Experimental Results Since there is a positive relationship between the display density and the BCR affinity, in order to detect the relationship between the display density of gB and the induced antibody titer, nanoparticles with different display densities are immunized at the same time to judge the influence of the display density on the immune effect of the nanoparticle. As shown in FIG. 11A to FIG. 11F, in detection of the antibody titer of the serum in the second week and the fifth week, the total antibody titers of the serum induced by the recombinant nanoparticles (gB-I53-50A NP) with the display densities (33%, 67% and 100%) were all higher than that of the monomer gB. The higher the display density was, the higher the total antibody titer of the serum was. Whether the aluminum adjuvant or the MF59 adjuvant is used, the total antibody titer of the serum induced by the gB nanoparticle (gB-I53-50A NP) is about 10 times greater than that of gB, and the result is also the same when no adjuvant is used. The use of the adjuvants can further enhance the immunogenicity induced by the recombinant nanoparticle.

Embodiment 6 Influence of Serum of Mice Immunized with Nanoparticle on Virus Infection Efficiency
1. Experimental Materials:
   (1) Reagents: Goat anti-human IgG (ThermoFisher), and other commercial and conventional reagents and consumables.
   (2) Cell lines: Akata-EBV-P (Vicbio (Beijing) Biotechnology Co., Ltd.), and HNE1(ATCC).
   (3) Virus: Akata-EBV-GFP virus induced by cell strain Akata-EBV.
2. Experimental Steps:
   (1) Akata-EBV was induced by IgG to produce the Akata-EBV-GFP virus, which was enriched by high-speed centrifugation, resuspended with serum-free 1640, and stored at −80° C.
   (2) The Akata virus was diluted by the serum-free 1640 culture medium (Gibco) with a ratio of 1:5, and added into 96-well plate, with 50 uL per well. The serum of the mice collected in the fifth week in Example 5 was diluted with a ratio of 1:5, then diluted into the virus with multiple proportions of 10, and incubated at 37° C. for 2 hours.
   (3) The mixture of the serum and the virus was added into spread HNE1 cells (7000 cells/well) and infected at 37° C. for 3.5 hours.
   (4) After infection, the supernatant was removed and replaced by 5% FBS 1640 culture medium. After culture for 48 hours, the cells were digested with pancreatin, and then the ratio of GFP positive cells to total cells was detected to judge the cell infection efficiency.

3. Experimental Results

Figure 12:
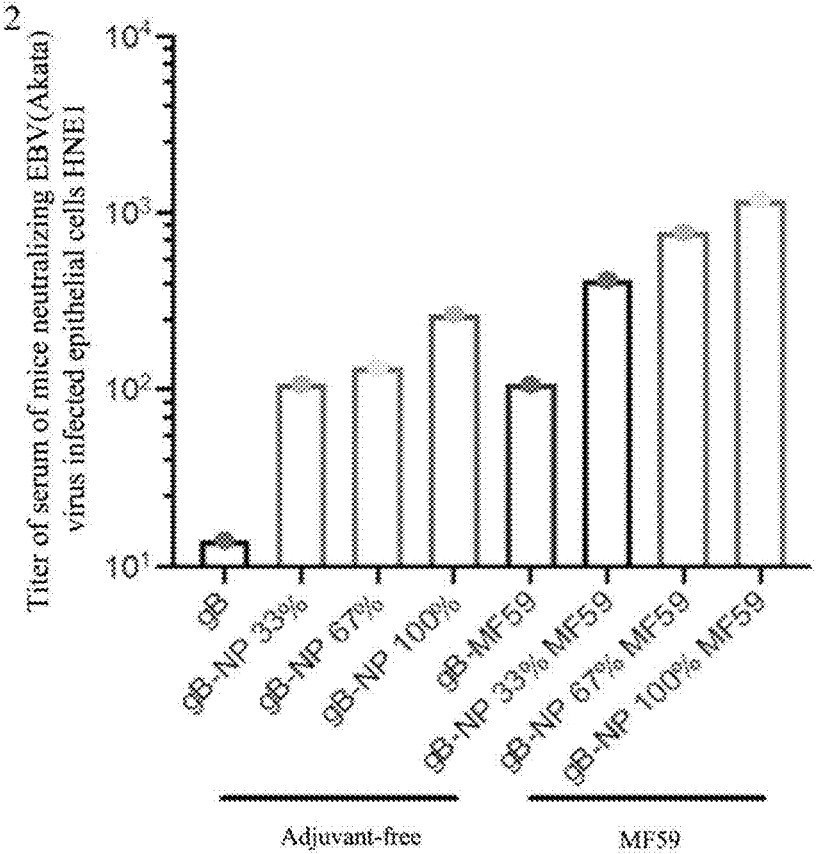
FIG. 12 is a graph showing influence of serum of mice immunized for five weeks on EBV-infected epithelial cells.

As shown in FIG. 12, gB-I53-50A NP with 33%, 67% and 100% display densities could all effectively produce a large number of neutralizing antibodies. Especially, the neutralizing antibody produced by gB with 100% display density has a titer that is about 10 times that of gB, which could effectively neutralize EBV infected epithelial cells. In addition, there was a more obvious difference in the ability to induce the neutralizing antibody in the adjuvant-free group.

The above examples are the preferred examples of the present disclosure, but the embodiments of the present disclosure are not limited by the above examples. Any other changes, modifications, substitutions, combinations, and simplifications made without departing from the spirit and principle of the present disclosure should be equivalent substitute modes, and should be included in the scope of protection of the present disclosure.

The invention claimed is:

1. A self-assembled nanoparticle, comprising a first polypeptide and a second polypeptide, wherein the first polypeptide comprises a gB protein and a first vector subunit, the second polypeptide comprises a second vector subunit; the first vector subunit is I53-50A1, and the second vector subunit is I53-50B.4PT1; and the gB protein is linked to the first vector subunit through a linker peptide;
wherein, the amino acid sequence of the I53-50A1 is SEQ ID NO: 1; the amino acid sequence of the I53-50B.4PT1 is SEQ ID NO: 2;
the amino acid sequence of the gB protein is SEQ ID NO: 3.

2. The self-assembled nanoparticle according to claim 1, wherein, the first polypeptide further comprises a stable protein; the stable protein is located between the first vector subunit and the linker peptide.

3. The self-assembled nanoparticle according to claim 2, wherein the first polypeptide is a part of a first polypeptide trimer, and the second polypeptide is a part of a second polypeptide pentamer.

4. The self-assembled nanoparticle according to claim 3, wherein there are 18 to 22 trimers in the nanoparticle and wherein there are 10 to 14 pentamers in the nanoparticle.

5. A preparation method of the self-assembled nanoparticle according to claim 1, comprising incubating the first polypeptide and the second polypeptide to obtain the self-assembled nanoparticle.

6. A vaccine, comprising the self-assembled nanoparticle according to claim 1.

7. The self-assembled nanoparticle according to claim 1, wherein the linker peptide is a polypeptide containing 5 amino acids to 20 amino acids.

8. The self-assembled nanoparticle according to claim 1, wherein the linker peptide is a polypeptide with the amino acid sequence of any one of SEQ ID NO: 4 to SEQ ID NO: 9.

9. The self-assembled nanoparticle according to claim 2, wherein the stable protein is T4 fibritin (SEQ ID NO: 10) or GCN4 peptide fragment (SEQ ID NO: 11).

10. The preparation method of the self-assembled nanoparticle according to claim 5, wherein the molar mass ratio of the first polypeptide to the second polypeptide is 1:(3).

11. The vaccine according to claim 6, further comprising an adjuvant.

12. A drug for preventing Epstein-Barr virus infection, comprising the self-assembled nanoparticle according to claim 1.

13. A method for preventing Epstein-Barr virus infection, comprising administering to a subject in need thereof an effective amount of the self-assembled nanoparticle according to claim 1.

14. A drug for treating diseases caused by Epstein-Barr virus infection, comprising the self-assembled nanoparticle according to claim 1.

15. A method for treating diseases caused by Epstein-Barr virus infection, comprising administering to a subject in need thereof an effective amount of the self-assembled nanoparticle according to claim 1.

* * * * *